United States Patent
Park et al.

(10) Patent No.: US 10,790,453 B2
(45) Date of Patent: Sep. 29, 2020

(54) COMPOUNDS AND ORGANIC ELECTRONIC DEVICE USING THE SAME

(71) Applicant: LG CHEM, LTD., Seoul (KR)

(72) Inventors: Tae Yoon Park, Daejeon (KR); Minseung Chun, Daejeon (KR); Dongheon Kim, Daejeon (KR); Jiyeon Ahn, Daejeon (KR); Hyoung Seok Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 213 days.

(21) Appl. No.: 15/495,646

(22) Filed: Apr. 24, 2017

(65) Prior Publication Data

US 2017/0229659 A1 Aug. 10, 2017

Related U.S. Application Data

(62) Division of application No. 14/345,887, filed as application No. PCT/KR2013/010873 on Nov. 27, 2013, now abandoned.

(30) Foreign Application Priority Data

Nov. 30, 2012 (KR) ........................ 10-2012-0138180

(51) Int. Cl.

| | |
|---|---|
| *H01L 51/50* | (2006.01) |
| *H01L 51/00* | (2006.01) |
| *C07D 403/04* | (2006.01) |
| *C09K 11/06* | (2006.01) |
| *C07D 403/10* | (2006.01) |
| *C07D 409/04* | (2006.01) |
| *C07D 239/70* | (2006.01) |
| *C07D 405/10* | (2006.01) |
| *C07D 405/04* | (2006.01) |
| *C07D 405/14* | (2006.01) |
| *C07D 401/14* | (2006.01) |
| *C07D 409/10* | (2006.01) |
| *C07D 409/14* | (2006.01) |
| *C09B 1/00* | (2006.01) |
| *C09B 57/00* | (2006.01) |
| *C09K 11/02* | (2006.01) |
| *H01L 51/52* | (2006.01) |

(52) U.S. Cl.
CPC ........ *H01L 51/0072* (2013.01); *C07D 239/70* (2013.01); *C07D 401/14* (2013.01); *C07D 403/04* (2013.01); *C07D 403/10* (2013.01); *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C09B 1/00* (2013.01); *C09B 57/00* (2013.01); *C09B 57/001* (2013.01); *C09K 11/025* (2013.01); *C09K 11/06* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/0052* (2013.01); *H01L 51/0073* (2013.01); *H01L 51/0085* (2013.01); *H01L 51/5012* (2013.01); *H01L 51/5016* (2013.01); *H01L 51/5072* (2013.01); *H01L 51/5092* (2013.01); *H01L 51/5096* (2013.01); *H01L 51/5206* (2013.01); *H01L 51/5221* (2013.01)

(58) Field of Classification Search
CPC ............ H01L 51/0067; H01L 51/0071; H01L 51/0072; H01L 51/0073; H01L 51/0074; H01L 51/50; H01L 51/5012; H01L 51/5016; H01L 51/5072; H01L 51/5092; H01L 51/5096; H01L 51/5206; H01L 51/5221; H01L 51/0052; H01L 51/0054; H01L 51/0058; C07D 239/70; C07D 403/04; C07D 403/10; C07D 409/04; C07D 409/10; C07D 405/04; C07D 405/10; C09K 11/06; C09K 2211/1011; C09K 2211/1044; C09K 2211/1048; C09K 2211/1051; C09K 2211/1007; C09K 2211/1029; C09K 2211/1088; C09K 2211/1092
USPC ...... 544/249, 294; 257/E51.049, E51.05, 40, 257/88–104, E51.001–E51.052; 428/690, 428/917, 691; 313/504, 506; 427/58, 66; 252/301.16–301.35
See application file for complete search history.

(56) References Cited

U.S. PATENT DOCUMENTS

| | | | |
|---|---|---|---|
| 4,769,378 | A | 9/1988 | Hirsch et al. |
| 5,594,001 | A | 1/1997 | Teleha et al. |

(Continued)

FOREIGN PATENT DOCUMENTS

| | | |
|---|---|---|
| CN | 87102424 A | 10/1987 |
| CN | 1295072 A | 5/2001 |

(Continued)

OTHER PUBLICATIONS

Mosher, et al.: "The Synthesis of 2,4-Diaryl-5H-indeni- and 2,4-Diaryl-5H-pyridocyclopenta[1,2-d]pyrimidin-5-ones", XP055280393, J. Org. Chem., vol. 36, No. 22, 1971, pp. 3382-3385.

(Continued)

*Primary Examiner* — Dylan C Kershner

(74) *Attorney, Agent, or Firm* — Dentons US LLP

(57) ABSTRACT

The present specification relates to an organic electronic device in which a novel compound that may improve a life-span, efficiency, a driving voltage drop, and stability of the organic electronic device is contained in an organic material layer.

7 Claims, 2 Drawing Sheets

(56) References Cited

U.S. PATENT DOCUMENTS

| | | | |
|---|---|---|---|
| 7,754,730 B2 | 7/2010 | Heintzelman et al. | |
| 8,309,564 B2 | 11/2012 | Gangjee | |
| 2002/0113545 A1* | 8/2002 | Adachi | H01L 51/5016 313/504 |
| 2010/0069647 A1 | 3/2010 | Suzuki | |
| 2012/0068170 A1 | 3/2012 | Pflumm | |
| 2014/0353650 A1* | 12/2014 | Shiomi | H05B 33/20 257/40 |
| 2015/0053936 A1* | 2/2015 | Takaku | H01L 51/0054 257/40 |
| 2015/0259347 A1 | 9/2015 | Park | |

FOREIGN PATENT DOCUMENTS

| | | |
|---|---|---|
| EP | 0 240 263 A2 | 10/1987 |
| JP | 1987-238275 A | 10/1987 |
| JP | 1996-509713 A | 10/1996 |
| JP | 2000-516206 | 12/2000 |
| JP | 2001-139556 A | 5/2001 |
| JP | 2013-041893 A | 2/2013 |
| KR | 10-2000-0051826 A | 8/2000 |
| KR | 10-2012-0044523 A | 5/2012 |
| WO | 93/08167 A1 | 4/1993 |
| WO | 9424131 A1 | 10/1994 |
| WO | 98/01449 | 1/1998 |
| WO | 2011-053508 A1 | 5/2011 |
| WO | 2013021907 A1 | 2/2013 |
| WO | WO-2013021907 A1 * | 2/2013 ......... H01L 51/0054 |
| WO | 2013180376 A1 | 12/2013 |
| WO | WO-2013180376 A1 * | 12/2013 ........... C07D 239/74 |

OTHER PUBLICATIONS

Caroti, A., et al., "Synthesis and Monoamine Oxidase Inhibitory Activity of New Pyridazine-, Pyrimidine- and 1,2,4-Triazine-Containing Tricyclic Derivatives," J. Med. Chem. 2007, vol. 50 (22), pp. 5364-5371.

Campaigne, E., et al., "Some Substituted 5H-Indeno [pyrimidines (1)," Journal of Heterocyclic Chemistry, 1970, vol. 7, pp. 937-940.

* cited by examiner

COMPOUNDS AND ORGANIC ELECTRONIC DEVICE USING THE SAME

CROSS-REFERENCE TO RELATED APPLICATIONS

This application is a divisional of U.S. application Ser. No. 14/345,887, filed Mar. 19, 2014, which is a National Stage Application of International Application No. PCT/KR2013/010873, filed Nov. 27, 2013, which claims priority to Korean Patent Application No. 10-2012-0138180, filed on Nov. 30, 2012, the disclosures of which are incorporated herein by reference in their entirety.

TECHNICAL FIELD

The present specification relates to an organic electronic device in which a novel compound that may improve a life-span, efficiency, a driving voltage drop, and stability of the organic electronic device is contained in an organic material layer.

BACKGROUND ART

An organic electronic device means a device that requires exchanging of electric charges between an electrode using holes and/or electrons and an organic material. The organic electronic device may be largely divided into the following two categories according to an operation principle. The first device is an electric device in which an exciton is formed in an organic material layer by a photon flowing from an external light source to the device, the exciton is separated into electrons and holes, and the electrons and the holes are transferred to the different electrodes and used as current sources (voltage sources). The second device is an electronic device in which holes and/or electrons are injected into an organic material semiconductor forming an interface in respect to an electrode by applying a voltage or a current to two or more electrodes, and operation is performed by the injected electrons and holes.

Examples of the organic electronic device include an organic electronic device, an organic solar cell, an organic photoconductor (OPC), an organic transistor, and the like, and all of the examples require a hole injection or transport material, an electron injection or transport material or a light emitting material in order to drive the device. Hereinafter, an organic light emitting device will be mainly described in detail, but in the organic electronic devices, the hole injection or transport material, the electron injection or transport material, or the light emitting material are operated based on a similar principle.

In general, an organic light emitting phenomenon means a phenomenon that converts electric energy into light energy by using an organic material. The organic electronic device using the organic light emitting phenomenon has a structure which generally includes an anode, a cathode, and an organic material layer disposed therebetween. Herein, the most organic material layers have a multilayered structure constituted by different materials in order to increase efficiency and stability of the organic electronic device, and may be formed of, for example, a hole injection layer, a hole transport layer, a light emitting layer, an electron transport layer, an electron injection layer, and the like. In the organic electronic device structure, if a voltage is applied between two electrodes, the holes are injected from the anode and the electrons are injected from the cathode to the organic material layer, and when the injected holes and electrons meet each other, an exciton is formed, and light is emitted when the exciton falls to a bottom state. It is known that this organic electronic device has characteristics such as self light emission, high brightness, high efficiency, a low driving voltage, a wide viewing angle, a high contrast, and a high speed response.

In the organic electronic device, the material used as the organic material layer may be classified into a light emitting material and an electric charge transport material, for example, a hole injection material, a hole transport material, an electron transport material, an electron injection material, and the like, according to a function thereof. Further, the light emitting material may be classified into blue, green, and red light emitting materials and yellow and orange light emitting materials required in order to implement better natural colors according to an emission color. Meanwhile, in the case where only one material is used as the light emitting material, since there are problems in that a maximum light emitting wavelength moves to a long wavelength or color purity is lowered due to interaction between molecules, or efficiency of the device is reduced due to a reduced effect of light emission, host/dopant systems may be used as the light emitting material in order to increase the color purity and increase light emitting efficiency through transferring of energy.

In order to allow the organic electronic device to sufficiently exhibit the aforementioned excellent characteristics, first, a material constituting the organic material layer in the device, for example, the hole injection material, the hole transport material, the light emitting material, the electron transport material, the electron injection material, and the like should be supported by stable and efficient materials, but the development of a stable and efficient organic material layer material for organic electronic devices has not yet been sufficiently made. Therefore, there is a continuous demand for developing a novel material, and the development of the material is similarly required for the aforementioned other organic electronic devices.

DISCLOSURE

Technical Problem

The present invention has been made in an effort to provide an organic electronic device including a compound that can satisfy conditions required in a material that may be used in the organic electronic device, for example, a life-span, efficiency, a driving voltage drop, stability, and the like, and has a chemical structure performing various roles required in the organic electronic device according to a substituent group.

Technical Solution

An exemplary embodiment of the present specification provides a compound represented by the following Chemical Formula 1.

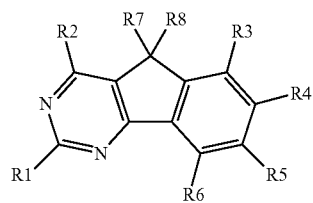

Chemical Formula 1

In Chemical Formula 1,

R1 to R8 are the same as or different from each other, and are each independently hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted heterocyclic group including one or more of N, O, and S atoms; or -L-A, L is a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, A is a substituted or unsubstituted aryl group; a substituted or unsubstituted carbazole group; a substituted or unsubstituted dibenzothiophene group; or a substituted or unsubstituted dibenzofuran group, at least one of R1 to R8 is -L-A, and R1 to R8 may form an aliphatic or hetero condensed cycle together with adjacent groups.

Another exemplary embodiment of the present specification provides an organic electronic device including a first electrode, a second electrode, and one or more organic material layers disposed between the first electrode and the second electrode, in which one or more layers of the organic material layers include the aforementioned compound.

Advantageous Effects

An organic electronic device according to an exemplary embodiment of the present specification has a merit in that a life-span characteristic is improved.

The organic electronic device according to the exemplary embodiment of the present specification has a merit in that light efficiency is improved.

The organic electronic device according to the exemplary embodiment of the present specification has a merit in that the organic electronic device has a low driving voltage.

The organic electronic device according to the exemplary embodiment of the present specification has a merit in that electrochemical stability and thermal stability are improved.

BEST MODE

Figure 1:
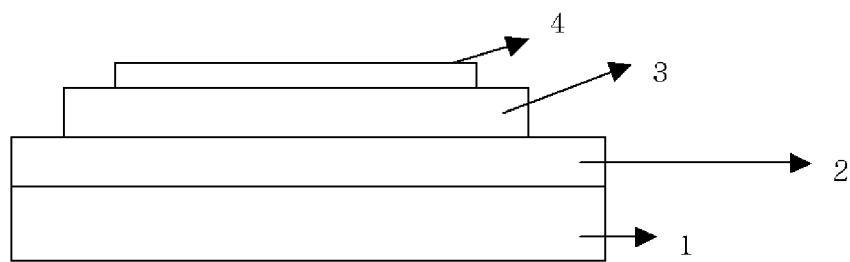
FIG. 1 illustrates an example of an organic electronic device including a substrate 1, an anode 2, a light emitting layer 3, and a cathode 4.

Hereinafter, the present specification will be described in more detail.

The present specification provides a nitrogen-containing heterocyclic compound.

The nitrogen-containing heterocyclic compound may be represented by Chemical Formula 1.

In Chemical Formula 1, at least one of R1 to R8 may include any one of a substituted or unsubstituted carbazole group, a substituted or unsubstituted dibenzothiophene group, and a substituted or unsubstituted dibenzofuran group.

For example, in Chemical Formula 1, at least one of R1 to R8 may be -L-A,

L may be a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, and A may be a substituted or unsubstituted aryl group; a substituted or unsubstituted carbazole group; a substituted or unsubstituted dibenzothiophene group; or a substituted or unsubstituted dibenzofuran group.

In Chemical Formula 1, at least one of R1 to R8 may be a substituted or unsubstituted carbazole group; a substituted or unsubstituted dibenzothiophene group; or a substituted or unsubstituted dibenzofuran group.

In Chemical Formula 1, R7 and R8 may be the same as or different from each other, and may be each independently a halogen group; a nitrile group; a nitro group; a hydroxy group; or a substituted or unsubstituted alkyl group.

In Chemical Formula 1, R7 and R8 may be the same as or different from each other, and may be each independently a substituted or unsubstituted alkyl group.

In Chemical Formula 1, R1 and R2 may be the same as or different from each other, and may be each independently a substituted or unsubstituted cycloalkyl group; a substituted or unsubstituted aryl group; a substituted or unsubstituted heterocyclic group including one or more of N, O, and S atoms; or a substituted or unsubstituted fluorenyl group.

In Chemical Formula 1, R1 and R2 may be the same as or different from each other, and may be each independently a substituted or unsubstituted heterocyclic group including one or more of N, O, and S atoms; or a substituted or unsubstituted aryl group.

In Chemical Formula 1, R1 and R2 may be the same as or different from each other, and may be each independently a substituted or unsubstituted pyridyl group; a substituted or unsubstituted pyrimidyl group; a substituted or unsubstituted pyrazinyl group; a substituted or unsubstituted phenyl group; a substituted or unsubstituted biphenyl group; a substituted or unsubstituted naphthyl group; or a substituted or unsubstituted tolyl group.

In Chemical Formula 1, at least one of R3 to R6 may include any one of a substituted or unsubstituted carbazole group; a substituted or unsubstituted dibenzothiophene group; and a substituted or unsubstituted dibenzofuran group.

In Chemical Formula 1, at least one of R3 to R6 may be -L-A,

L may be a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, and A may be a substituted or unsubstituted aryl group; a substituted or unsubstituted carbazole group; a substituted or unsubstituted dibenzothiophene group; or a substituted or unsubstituted dibenzofuran group.

In Chemical Formula 1, R1 and R2 may be the same as or different from each other, and may be each independently a substituted or unsubstituted cycloalkyl group; a substituted or unsubstituted aryl group; a substituted or unsubstituted heterocyclic group including one or more of N, O, and S atoms; or a substituted or unsubstituted fluorenyl group, at least one of R3 to R6 may be -L-A, L may be a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, A may be a substituted or unsubstituted aryl group; a substituted or unsubstituted carbazole group; a substituted or unsubstituted dibenzothiophene group; or a substituted or unsubstituted dibenzofuran group, R7 and R8 may be the same as or different from each other, and may be each independently a halogen group; a nitrile group; a nitro group; a hydroxy group; or a substituted or unsubstituted alkyl group.

In Chemical Formula 1, R7 and R8 may be the same as or different from each other, and may be each independently a substituted or unsubstituted alkyl group.

In Chemical Formula 1, R1 and R2 may be each independently a phenyl group, a biphenyl group, a tolyl group, a naphthyl group, a pyridyl group, a pyrimidyl group, a pyrazinyl group, or a fluorenyl group, R3 to R6 may be each independently hydrogen; heavy hydrogen; a halogen group; a nitrile group; a nitro group; a hydroxy group; a substituted or unsubstituted alkyl group; or -L-A, L may be a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, A may be a substituted or unsubstituted aryl group; a substituted or unsubstituted carbazole group; a substituted or unsubstituted dibenzothiophene group; or a substituted or unsubstituted dibenzofuran group, at least one of R3 to R6 may be -L-A, and R7 and R8 may be the same as or different from each other, and may be each independently a substituted or unsubstituted alkyl group.

In Chemical Formula 1, any one of R1 and R2 may be -L-A, and the other may be a substituted or unsubstituted cycloalkyl group; a substituted or unsubstituted aryl group; a substituted or unsubstituted heterocyclic group including one or more of N, O, and S atoms; or a substituted or unsubstituted fluorenyl group.

In Chemical Formula 1, at least one of R1, R2, R4, and R5 may be -L-A.

In Chemical Formula 1, at least one of R1, R2, R4, and R5 may be -L-A, the others may be the same as or different from each other, and may be each independently a substituted or unsubstituted cycloalkyl group; a substituted or unsubstituted aryl group; a substituted or unsubstituted heterocyclic group including one or more of N, O, and S atoms; or a substituted or unsubstituted fluorenyl group.

In Chemical Formula 1, at least one of R1, R2, R4, and R5 may be -L-A, and the others may be the same as or different from each other, and may be each independently a substituted or unsubstituted cycloalkyl group; a substituted or unsubstituted aryl group; a substituted or unsubstituted heterocyclic group including one or more of N, O, and S atoms; or a substituted or unsubstituted fluorenyl group, R3 and R6 may be hydrogen, R7 and R8 may be each independently a substituted or unsubstituted alkyl group.

In Chemical Formula 1, any one of R2, R4, and R5 may be -L-A.

In an exemplary embodiment of the present specification, the compound represented by Chemical Formula 1 may be represented by the following Chemical Formula 2.

Chemical Formula 2

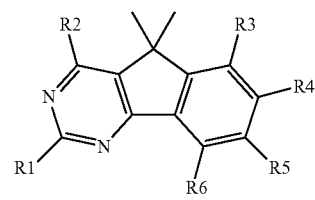

In Chemical Formula 2,

R1 to R6 are the same as or different from each other, and are each independently hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; a substituted or unsubstituted dibenzothiophene group; a substituted or unsubstituted dibenzofuran group; a substituted or unsubstituted heterocyclic group including one or more of N, O, and S atoms; or -L-A, L is a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, A is a substituted or unsubstituted aryl group; a substituted or unsubstituted carbazole group; a substituted or unsubstituted dibenzothiophene group; or a substituted or unsubstituted dibenzofuran group, at least one of R1 to R6 is -L-A, and R1 to R6 may form an aliphatic or hetero condensed cycle together with adjacent groups.

In the exemplary embodiment of the present specification, the compound represented by Chemical Formula 1 may be represented by the following Chemical Formula 2.

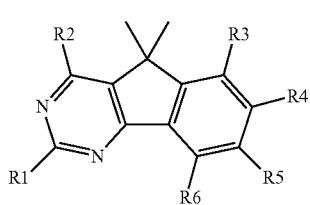

Chemical Formula 2

In Chemical Formula 2, R1 and R2 are each independently a phenyl group, a biphenyl group, a tolyl group, a naphthyl group, a pyridyl group, a pyrimidyl group, a pyrazinyl group, or a fluorenyl group, R3 to R6 are each independently hydrogen; heavy hydrogen; a halogen group; a nitrile group; a nitro group; a hydroxy group; a substituted or unsubstituted alkyl group; or -L-A, L is a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, A is a substituted or unsubstituted aryl group; a substituted or unsubstituted carbazole group; a substituted or unsubstituted dibenzothiophene group; or a substituted or unsubstituted dibenzofuran group, and at least one of R3 to R6 is -L-A.

In Chemical Formula 1 or 2, the aryl group of A may be a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenalenyl group; a substituted or unsubstituted naphthacenyl group; a substituted or unsubstituted pentacenyl group; a substituted or unsubstituted phenanthrenyl group; a substituted or unsubstituted pyrenyl group; a substituted or unsubstituted triphenylenyl group; a substituted or unsubstituted fluoranthenyl group; a substituted or unsubstituted perylenyl group; or a substituted or unsubstituted chrysenyl group.

In the compound according to the present specification, substituent groups of Chemical Formula 1 will be described in more detail below.

In the present specification, examples of the halogen group may include fluorine, chlorine, bromine, iodine, and the like, but are not limited thereto.

In the present specification, the alkyl group may be a straight or branched chain, and the number of carbon atoms thereof is not particularly limited but is preferably 1 to 12. Specific examples thereof include a methyl group, an ethyl group, a propyl group, an isopropyl group, a butyl group, a t-butyl group, a pentyl group, a hexyl group, a heptyl group, and the like, but are not limited thereto.

In the present specification, the cycloalkyl group is not particularly limited, but the number of carbon atoms thereof is preferably 3 to 60, and specific examples thereof may include a cyclopentyl group, a cyclohexyl group, and the like.

In the present specification, the alkenyl group may be a straight or branched chain, and the number of carbon atoms thereof is not particularly limited but is preferably 2 to 12. Specific examples thereof include an alkenyl group to which an aryl group, such as a butenyl group; a pentenyl group; a stylbenyl group, and a styrenyl group, is connected, but are not limited thereto.

In the present specification, it is preferable that the alkoxy group have 1 to 12 carbon atoms, and more specific examples thereof may include methoxy, ethoxy, isopropyloxy, and the like, but are not limited thereto.

In the present specification, the aryl group may be monocyclic or polycyclic, and the number of carbon atoms thereof is not particularly limited but is preferably 6 to 40. Examples of the monocyclic aryl group may include a phenyl group, a biphenyl group, a terphenyl group, stilben, and the like, and examples of the polycyclic aryl group may include a naphthyl group, an anthracenyl group, a phenalenyl group, a naphthacenyl group, a pentacenyl group, a phenanthrenyl group, a pyrenyl group, a triphenylenyl group, a fluoranthenyl group, a perylenyl group, a chrysenyl group, a fluorenyl group, and the like, but are not limited thereto.

In the present specification, the fluorenyl group has a structure where two cyclic organic compounds are connected through one atom, and examples thereof include

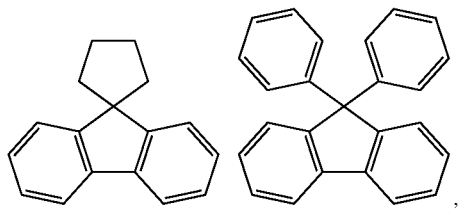

and the like.

In the present specification, the fluorenyl group includes a structure of an opened fluorenyl group, the opened fluorenyl group has a structure where two cyclic compounds are connected through one atom and connection of one cyclic compound is broken, and examples thereof include

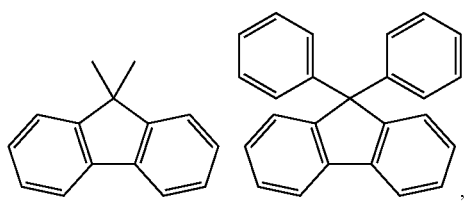

and the like.

In the present specification, the number of carbon atoms of the amine group is not particularly limited, but preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of the arylamine group mean a substituted or unsubstituted monocyclic diarylamine group, a substituted or unsubstituted polycyclic diarylamine group, or a substituted or unsubstituted monocyclic and polycyclic diarylamine group.

In the present specification, the heterocyclic group is a heterocyclic group including one or more of N, O, and S atoms as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazolee group, a benzimidazole group, a benzthiazol group, a benzcarbazole group, a benzthiophene group, a dibenzothiophene group, a benzfuranyl group, a dibenzofuranyl group, and the like, but are not limited thereto.

For example, the heterocyclic group is preferably compounds of the following Structural Formulas, but is not limited thereto.

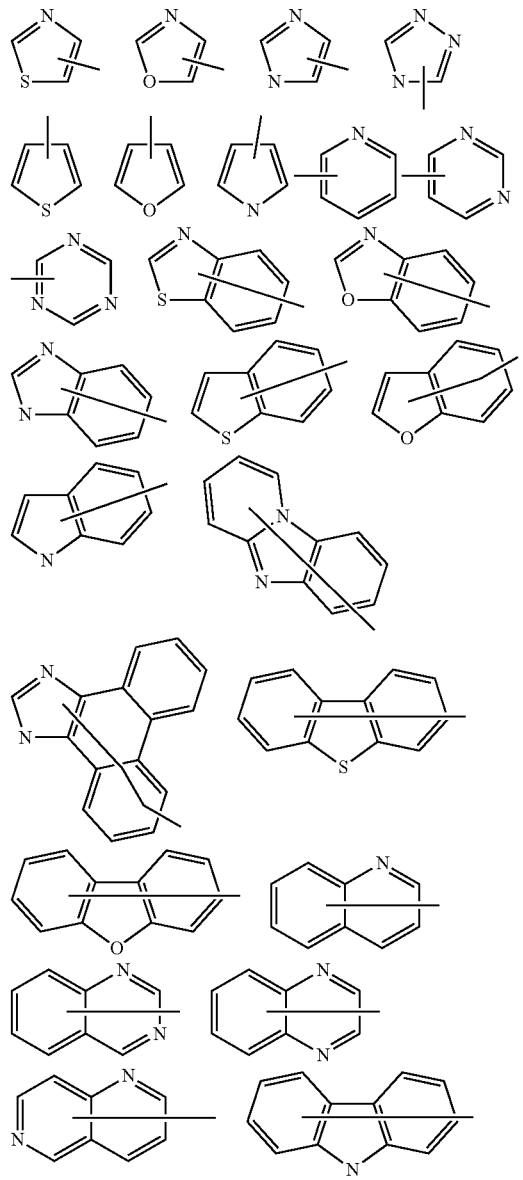

In the present specification, the aryl group of the aryloxy group, the arylthioxy group, the arylsulfoxy group, and the aralkylamine group is the same as the aforementioned examples of the aryl group.

In the present specification, the alkyl group of the alkylthioxy group, the alkylsulfoxy group, the alkylamine group, and the aralkylamine group is the same as the aforementioned examples of the alkyl group.

In the present specification, the heteroaryl group of the heteroarylamine group may be selected from the aforementioned examples of the heterocyclic group.

Further, in the present specification, the term "substituted or unsubstituted" means that substitution is performed by one or more substituent groups selected from the group consisting of heavy hydrogen, a halogen group, an alkyl group, an alkenyl group, an alkoxy group, a silyl group, an arylalkenyl group, an aryl group, a heteroaryl group, a carbazole group, an arylamine group, a fluorenyl group, and a nitrile group, or there is no substituent group.

In the exemplary embodiment of the present specification, the compound represented by Chemical Formula 1 may be represented by any one of the following Chemical Formulas, but is not limited thereto.

[Chemical Formula 1-1]

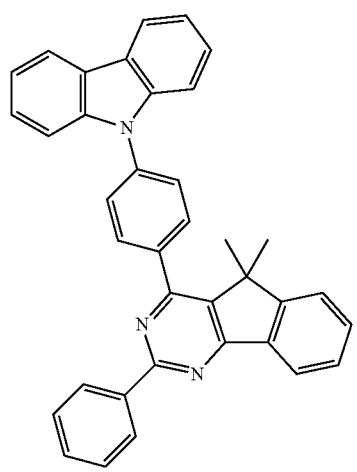

[Chemical Formula 1-2]

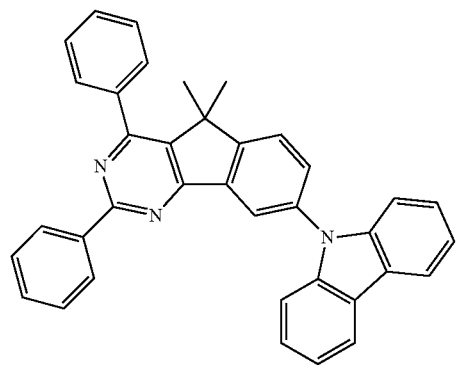

[Chemical Formula 1-3]

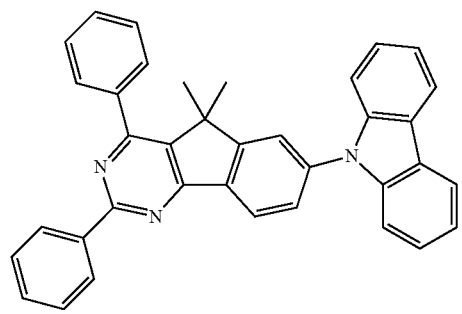

[Chemical Formula 1-4]

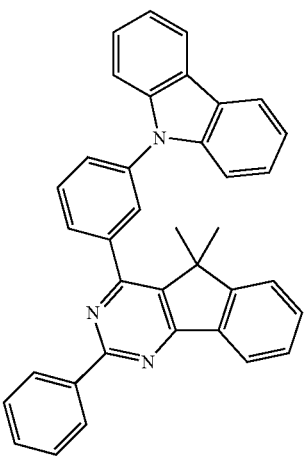

[Chemical Formula 1-5]

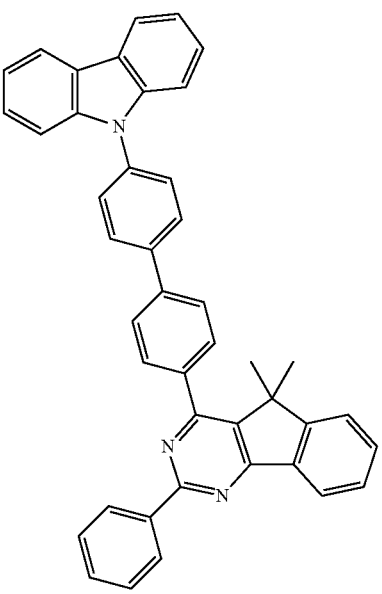

[Chemical Formula 1-6]

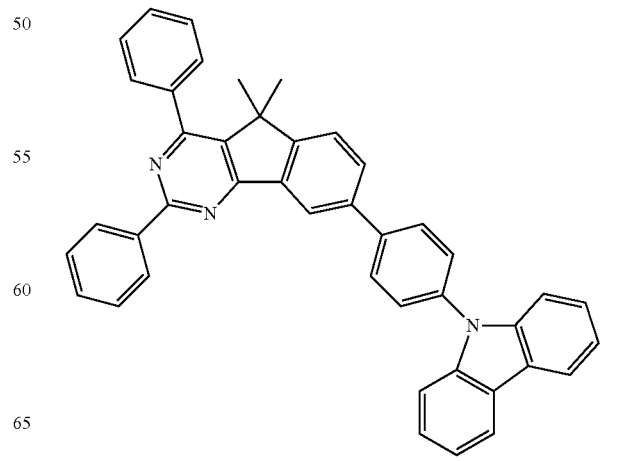

[Chemical Formula 1-7]
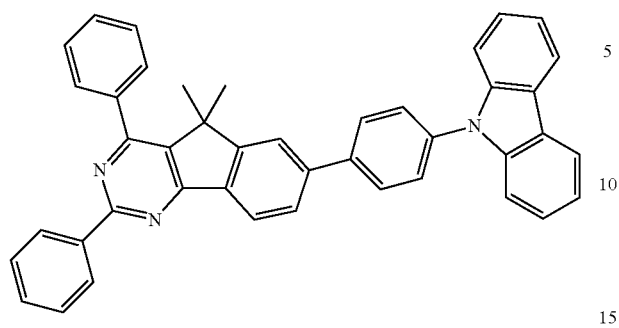
[Chemical Formula 1-8]
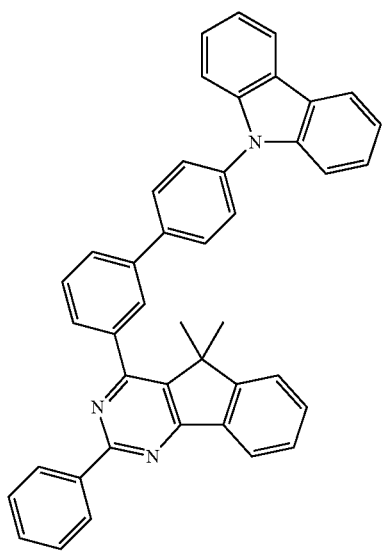
[Chemical Formula 1-9]
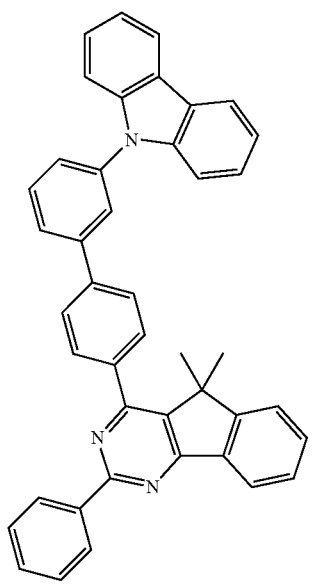
[Chemical Formula 1-10]
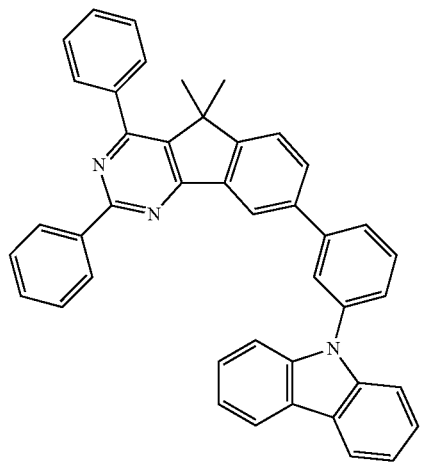
[Chemical Formula 1-11]
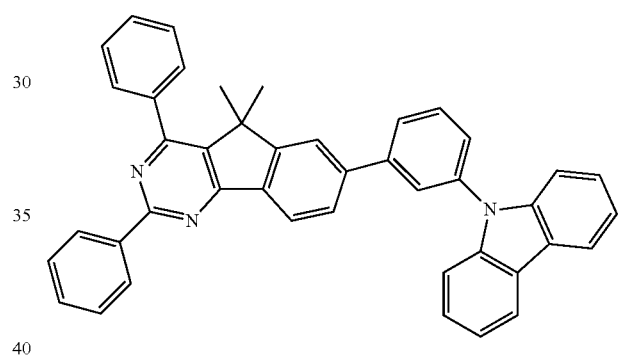
[Chemical Formula 1-12]
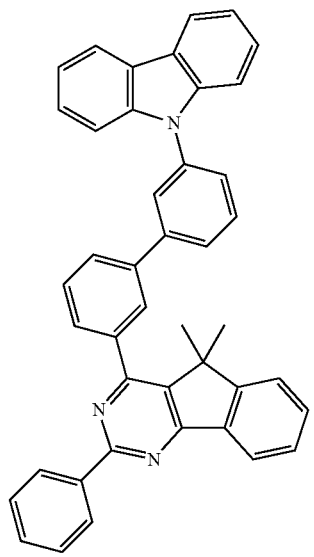

[Chemical Formula 1-13]
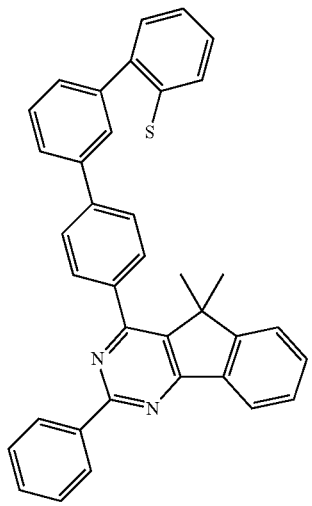
[Chemical Formula 1-14]
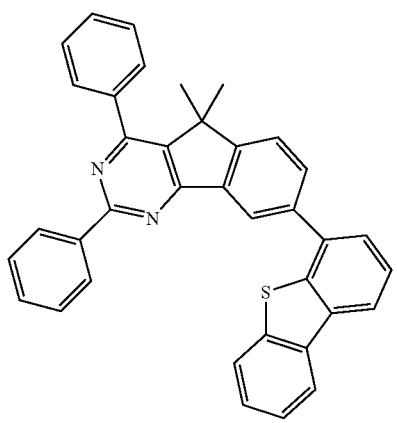
[Chemical Formula 1-15]
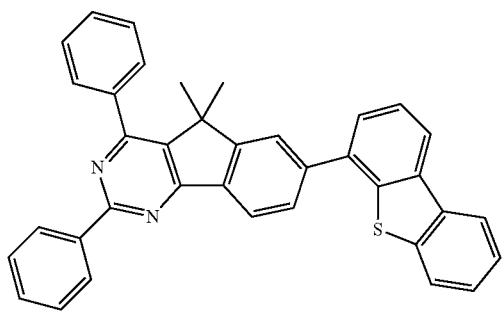
[Chemical Formula 1-16]
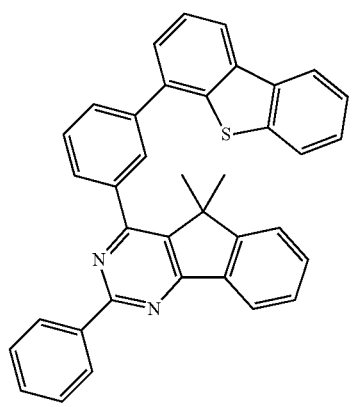
[Chemical Formula 1-17]
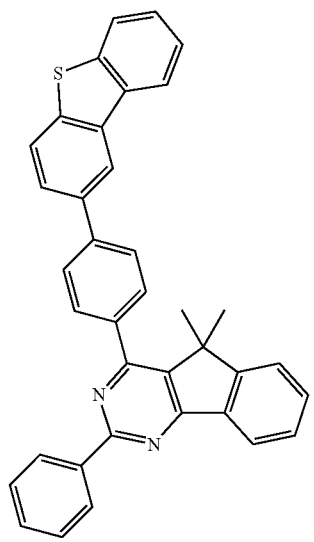
[Chemical Formula 1-18]
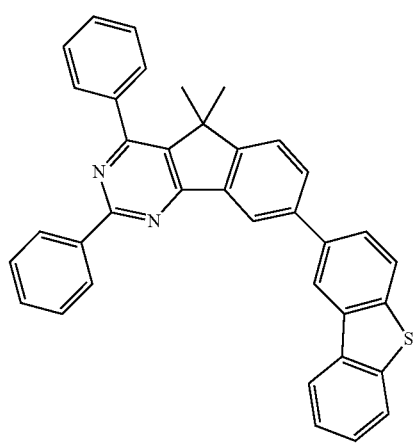

[Chemical Formula 1-19]
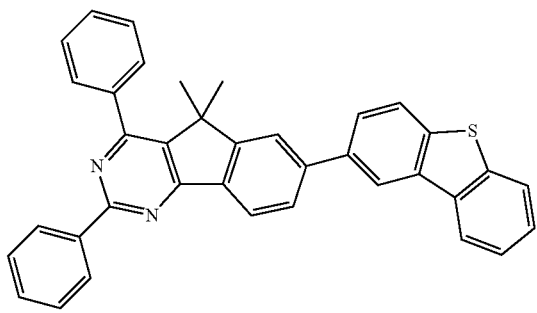
[Chemical Formula 1-20]
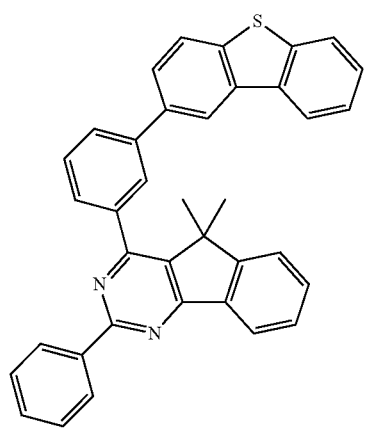
[Chemical Formula 1-21]
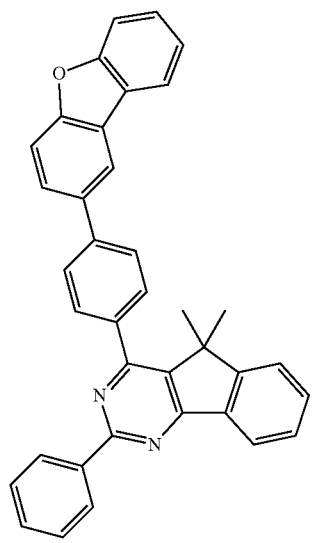
[Chemical Formula 1-22]
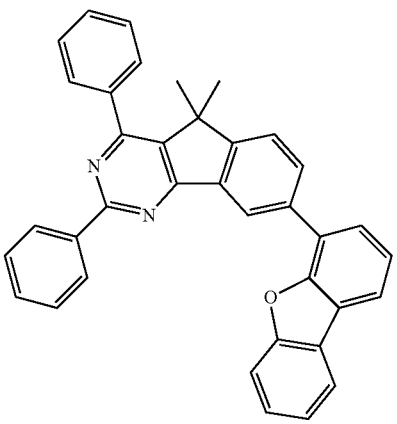
[Chemical Formula 1-23]
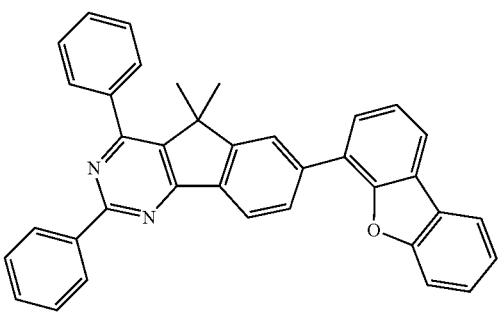
[Chemical Formula 1-24]
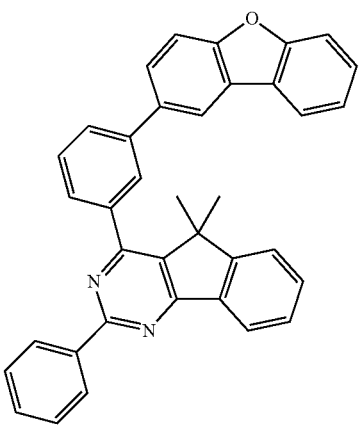

[Chemical Formula 1-25]
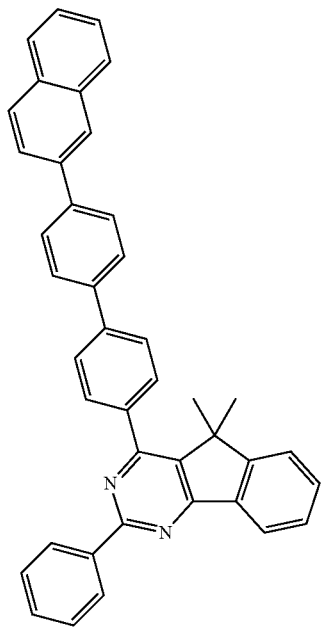
[Chemical Formula 1-26]
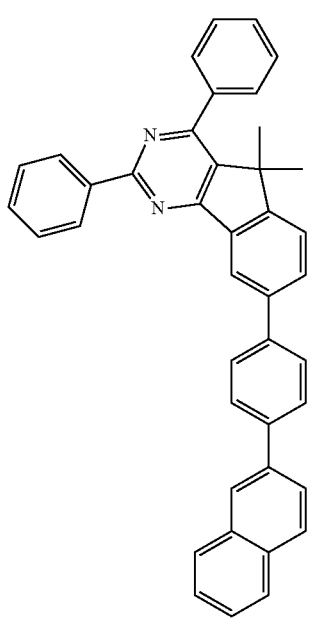
[Chemical Formula 1-27]
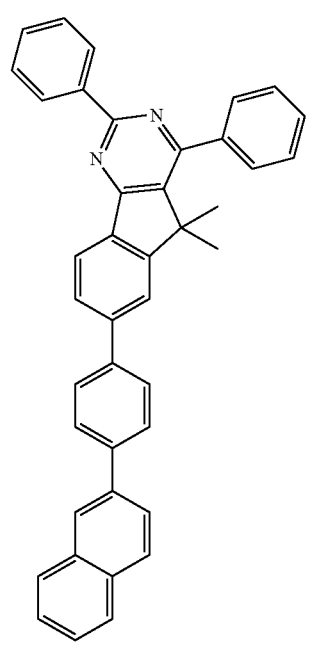
[Chemical Formula 1-28]

[Chemical Formula 1-29]
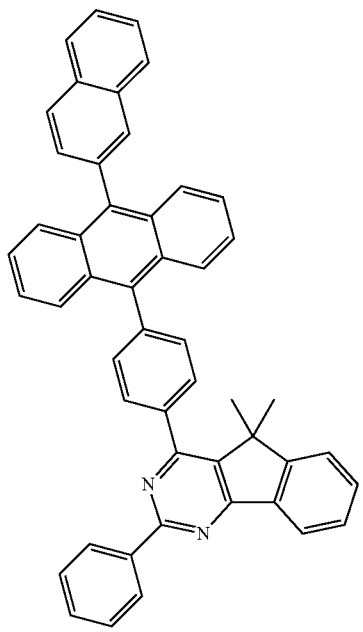
[Chemical Formula 1-30]
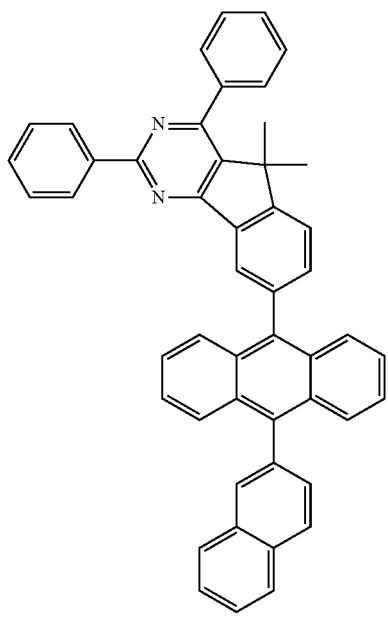
[Chemical Formula 1-31]
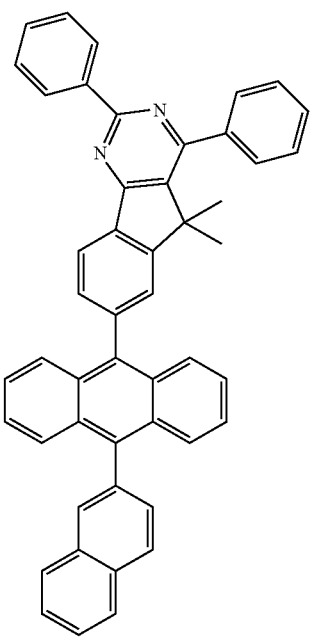
[Chemical Formula 1-32]
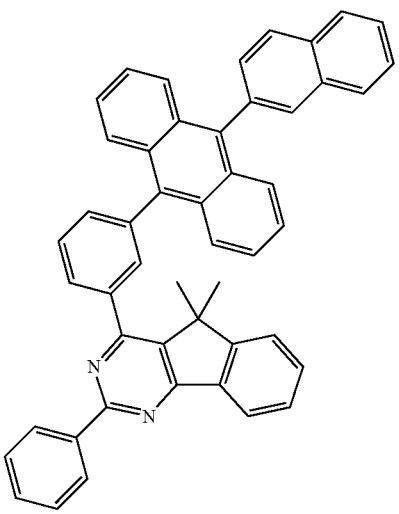

[Chemical Formula 1-33]
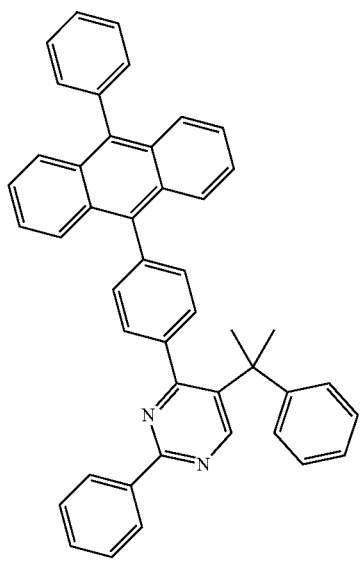
[Chemical Formula 1-34]
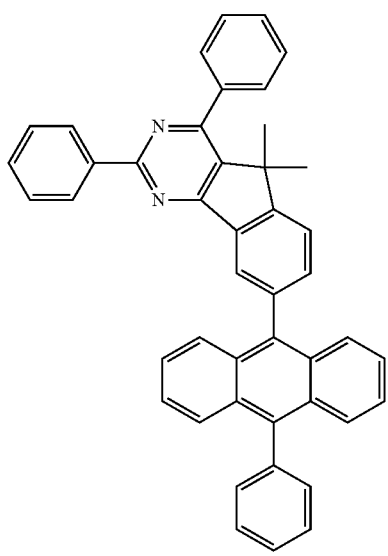
[Chemical Formula 1-35]
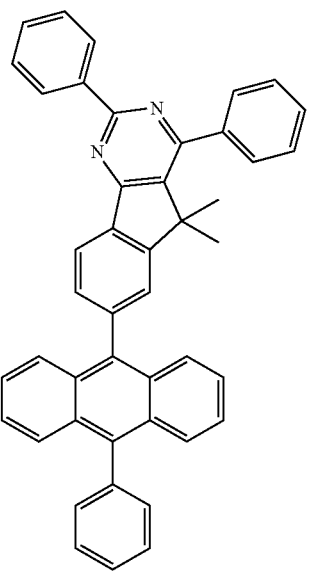
[Chemical Formula 1-36]
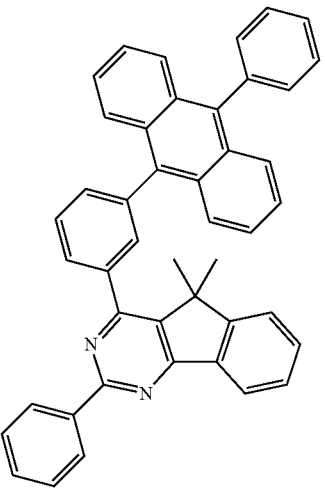

[Chemical Formula 1-37]
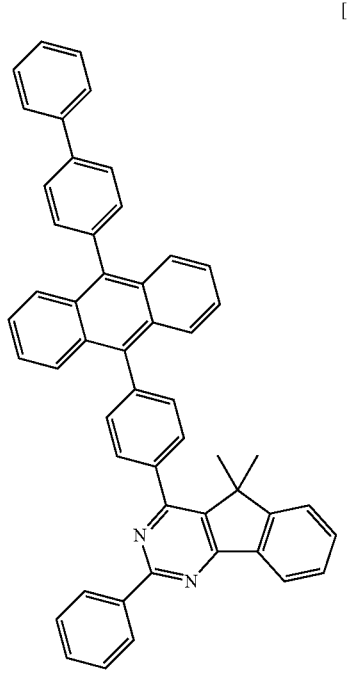
[Chemical Formula 1-38]
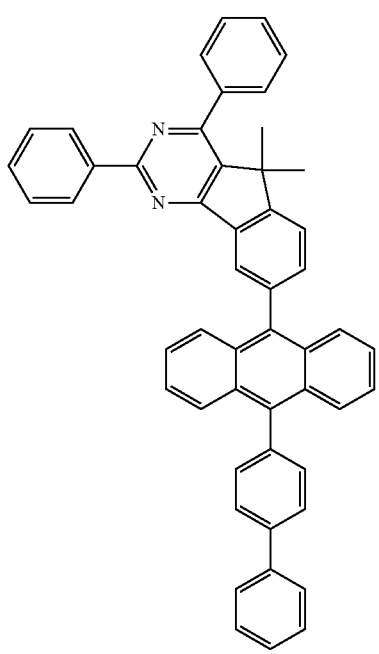
[Chemical Formula 1-39]
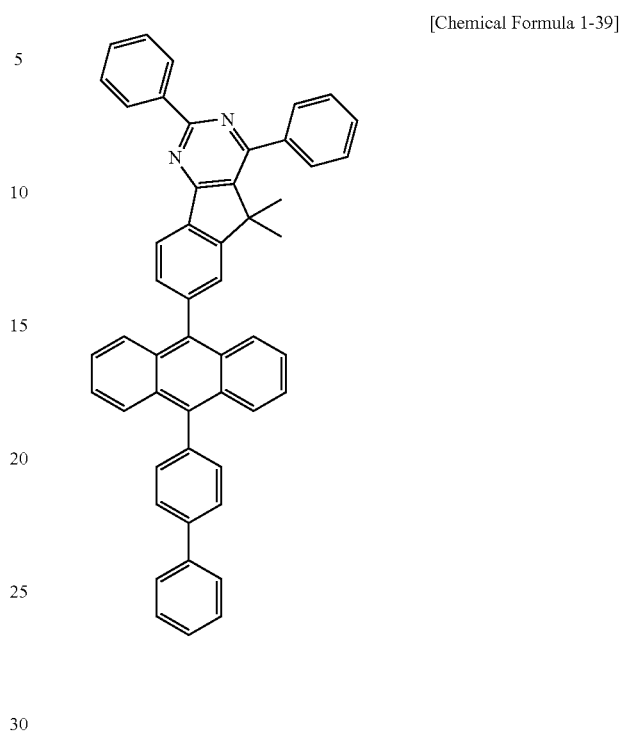
[Chemical Formula 1-40]
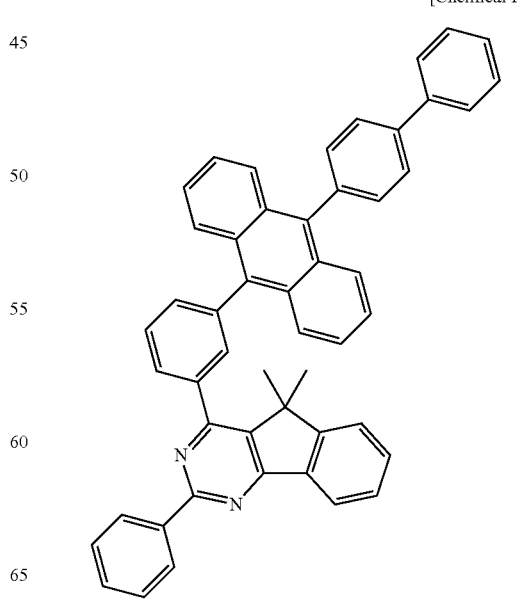

[Chemical Formula 1-41]
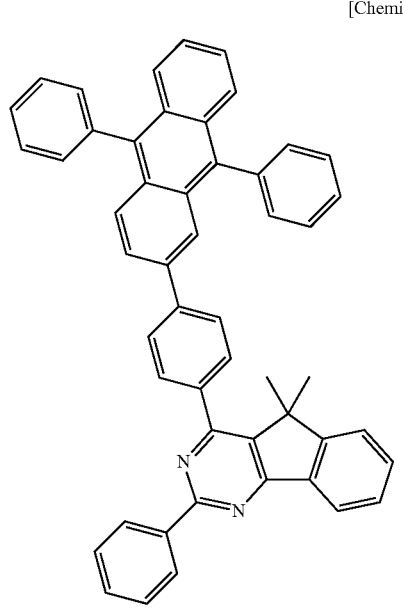
[Chemical Formula 1-43]
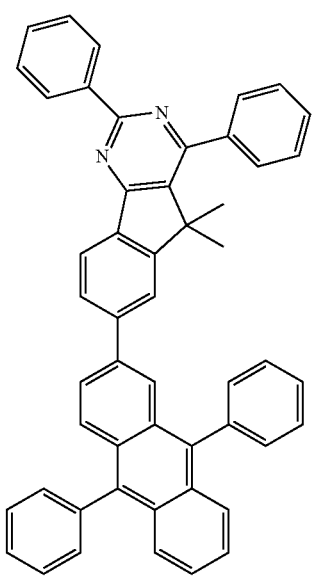
[Chemical Formula 1-42]
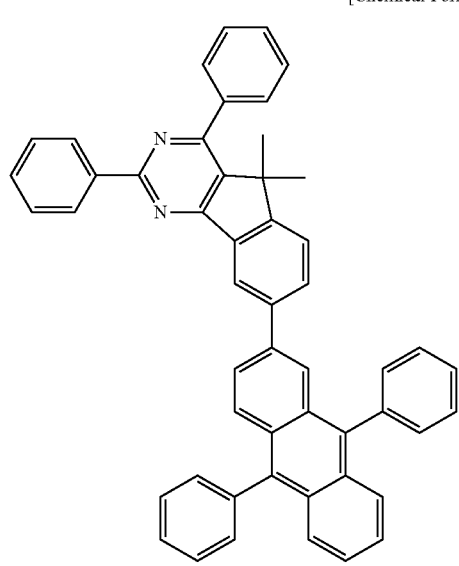
[Chemical Formula 1-44]
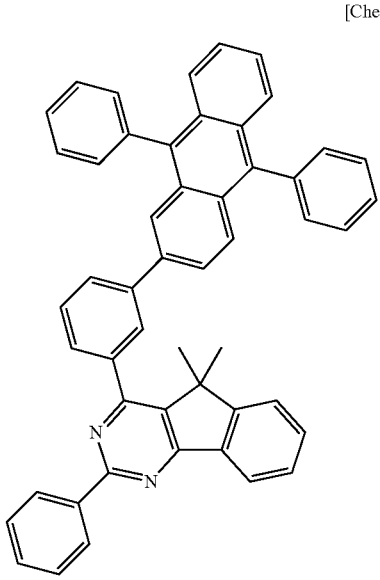

[Chemical Formula 1-45]
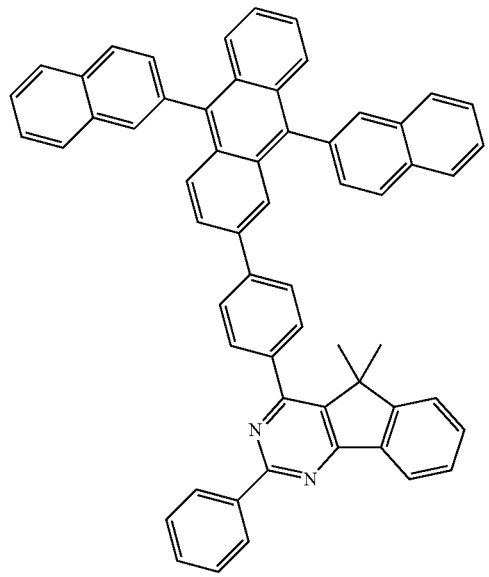
[Chemical Formula 1-46]
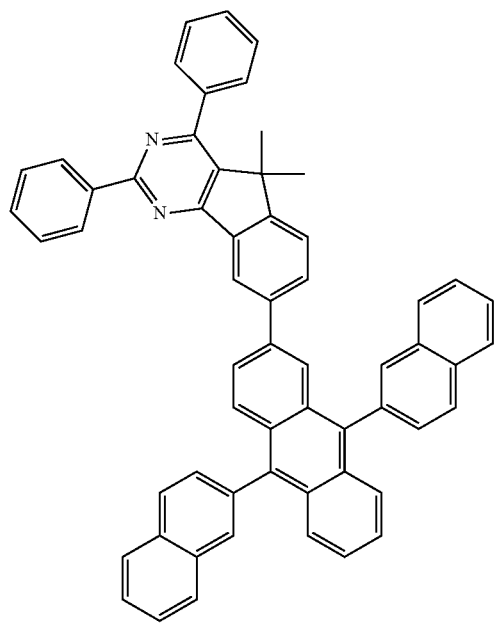
[Chemical Formula 1-47]
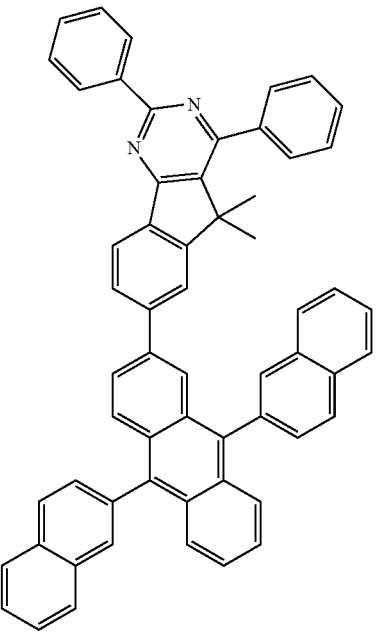
[Chemical Formula 1-48]
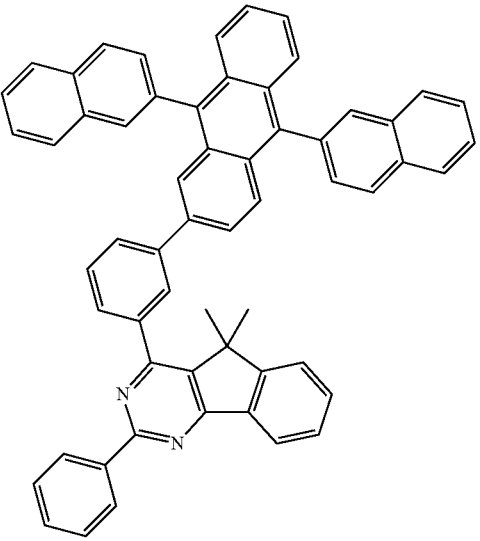

[Chemical Formula 1-49]
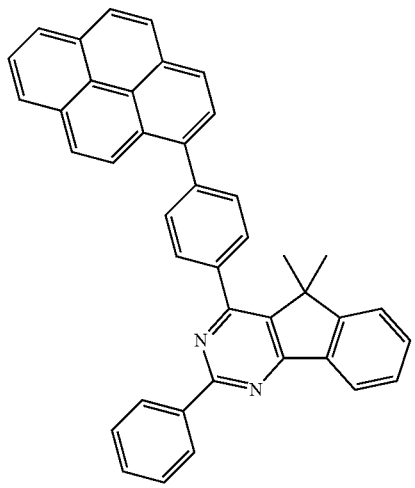
[Chemical Formula 1-50]
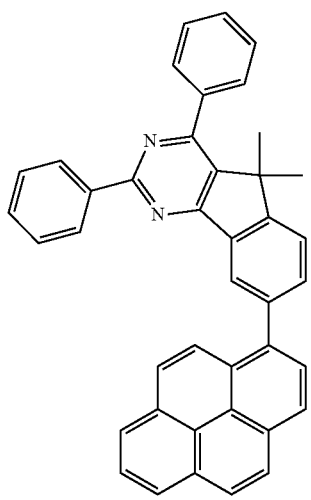
[Chemical Formula 1-51]
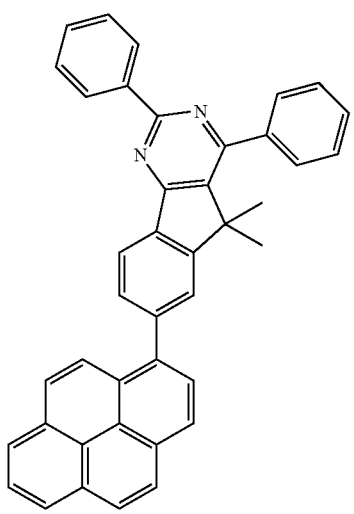
[Chemical Formula 1-52]
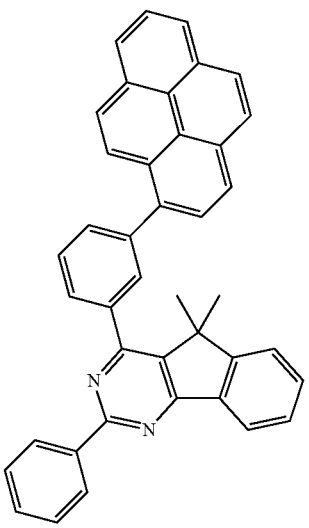
[Chemical Formula 1-53]
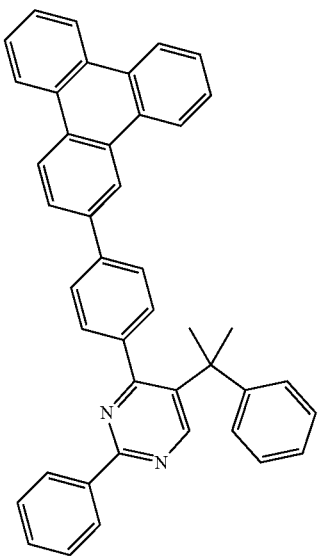
[Chemical Formula 1-54]
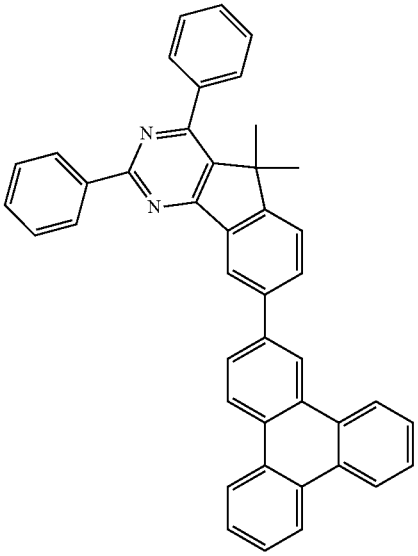

[Chemical Formula 1-55]
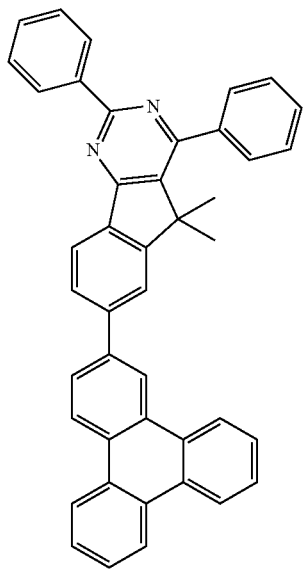
[Chemical Formula 1-56]
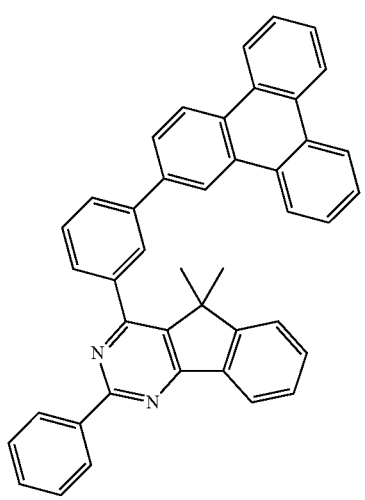
[Chemical Formula 1-57]
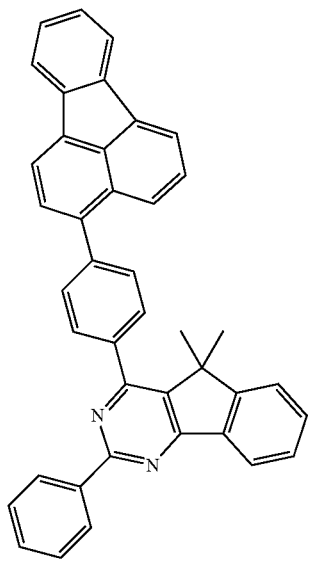
[Chemical Formula 1-58]
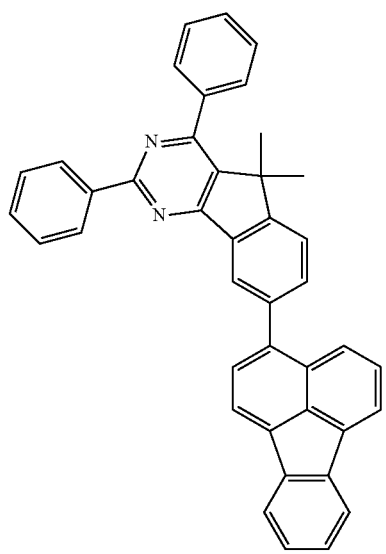
[Chemical Formula 1-59]
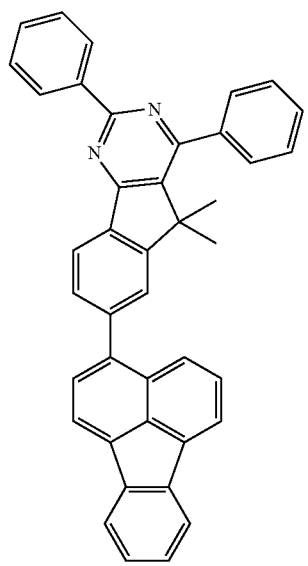
[Chemical Formula 1-60]
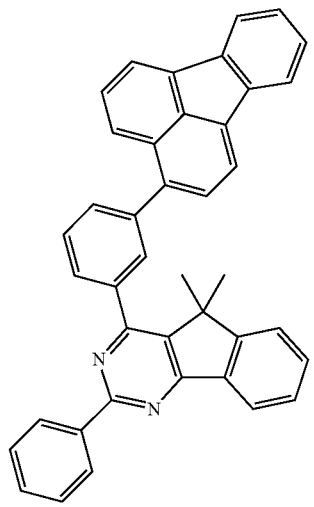

[Chemical Formula 1-61]
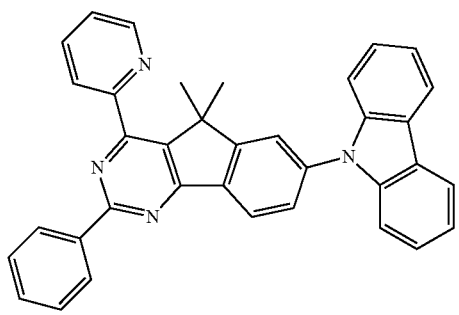
[Chemical Formula 1-62]
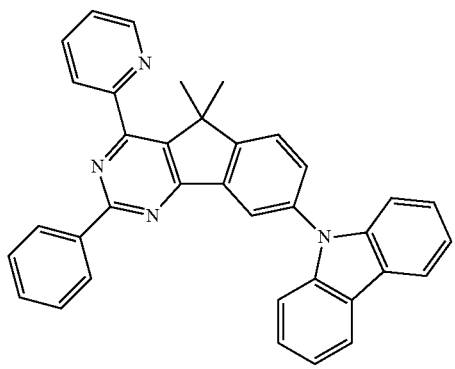
[Chemical Formula 1-63]
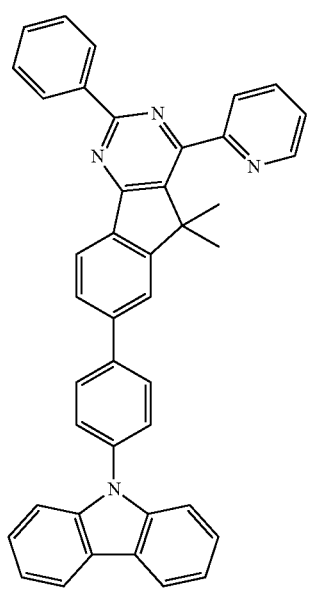
[Chemical Formula 1-64]
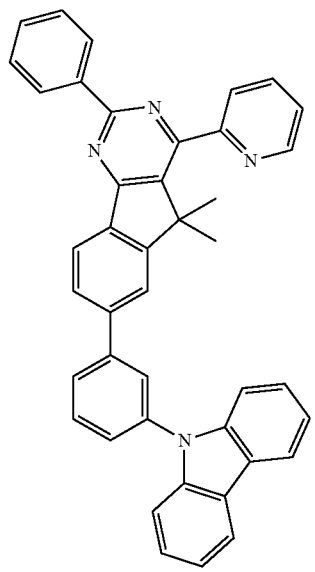
[Chemical Formula 1-65]
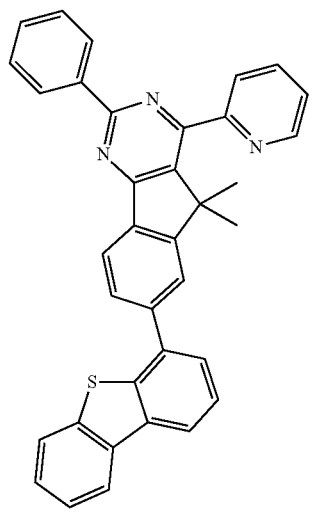
[Chemical Formula 1-66]
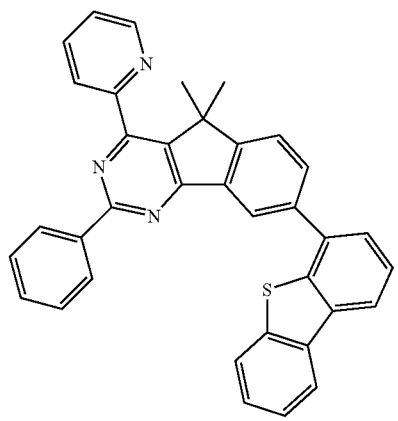

[Chemical Formula 1-67]

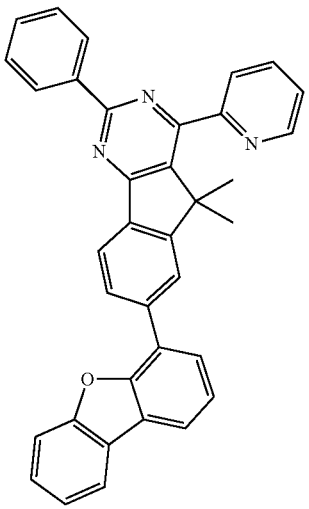

[Chemical Formula 1-68]

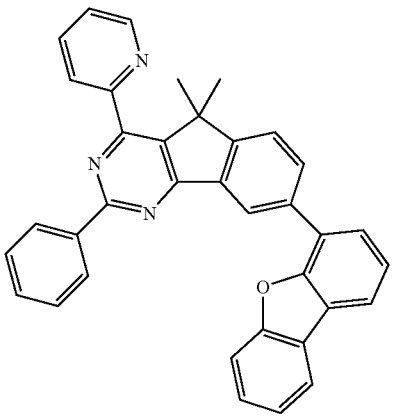

The novel compound according to the present specification has a merit in that thermal stability is excellent.

The novel compound according to the present specification has a merit in that the novel compound has a deep HOMO level.

The novel compound according to the present specification has a merit in that the novel compound has a high triplet state.

The novel compound according to the present specification has a merit in that the novel compound has hole stability.

The novel compound according to the present specification may be purely used or used while being mixed with an impurity in the organic electronic device including a light emitting device.

Since the compound includes an amine structure in a core structure, the compound may have an appropriate energy level as hole injection and/or hole transport materials in the organic electronic device. In the present specification, a device having a low driving voltage and high light efficiency may be implemented by selecting the compound having the appropriate energy level according to the substituent group among the aforementioned compounds and using the selected compound in the organic electronic device.

Further, an energy band gap may be finely controlled, and a characteristic at an interface between organic materials may be improved, by introducing various substituent groups to the core structure, and thus the purpose of the material may be diversified.

Meanwhile, the compound represented by Chemical Formula 1 has a high glass transition temperature (Tg), and thus thermal stability is excellent. Such an increase in thermal stability becomes an important factor providing driving stability to the device.

The organic electronic device according to the present specification has a merit in that light efficiency is improved and a life-span characteristic of the device is improved due to high thermal stability.

Further, the organic electronic device according to the present specification is an organic electronic device including a first electrode, a second electrode, and one or more organic material layers disposed between the first electrode and the second electrode, and one or more layers of the organic material layers include the compound represented by Chemical Formula 1.

Examples of the organic electronic device include an organic light emitting device, an organic solar cell, an organic photoconductor (OPC), an organic transistor, and the like, but are not limited thereto.

The organic electronic device of the present specification may be manufactured by a general manufacturing method and a general material of the organic electronic device, except that one or more organic material layers are formed by using the compound represented by Chemical Formula 1.

The compound represented by Chemical Formula 1 may be formed as the organic material layer by a solution coating method as well as a vacuum deposition method when the organic electronic device is manufactured. Herein, the solution coating method means spin coating, dip coating, inkjet printing, screen printing, a spray method, roll coating, or the like, but is not limited thereto.

The organic material layer of the organic electronic device of the present specification may have a single layer structure, but may have a multilayered structure in which two or more organic material layers are laminated. For example, the organic electronic device of the present specification may have a structure including a hole injection layer, a hole transport layer, a light emitting layer, an electron transport layer, an electron injection layer, and the like as the organic material layer. However, the structure of the organic electronic device is not limited thereto, but may include the smaller number of organic material layers.

Accordingly, in the organic electronic device of the present specification, the organic material layer may include one or more layers of the hole injection layer, the hole transport layer, and a layer injecting and transporting holes simultaneously, and one or more layers of the layers may include the compound represented by Chemical Formula 1.

Further, the organic material layer may include the light emitting layer, and the light emitting layer may include the compound represented by Chemical Formula 1.

Further, the organic material layer may include one or more layers of an electron blocking layer, the electron transport layer, the electron injection layer, and a layer transporting and injecting electrons simultaneously, and one or more layers of the layers may include the compound represented by Chemical Formula 1.

Further, the compound of the present specification may be used as an organic material layer material, particularly a hole transport layer material, an electron blocking layer material, a material of a layer transporting the holes and blocking the electrons simultaneously, a phosphorescence light emitting layer material, or the like in the organic electronic device.

In the organic material layer having the multilayered structure, the compound represented by Chemical Formula 1 may be included in the light emitting layer, the layer transporting the holes/blocking the electrons simultaneously, a layer injecting the holes/transporting the holes and emitting light simultaneously, a layer transporting the holes and emitting light simultaneously, or a layer transporting the electrons and emitting light simultaneously, and the like.

For example, the organic electronic device according to the present specification may be manufactured by depositing metal, metal oxides having conductivity, or an alloy thereof on a substrate by using a PVD (physical vapor deposition) method such as sputtering or e-beam evaporation to form an anode, forming the organic material layer including the hole injection layer, the hole transport layer, the light emitting layer, and the electron transport layer thereon, and then depositing a material, which may be used as a cathode, thereon. In addition to the aforementioned method, the organic electronic device may be manufactured by sequentially depositing a cathode material, the organic material layer, and an anode material on the substrate.

The organic material layer may have the multilayered structure including the hole injection layer, the hole transport layer, the light emitting layer, the electron transport layer, and the like, but is not limited thereto and may have a single layer structure. Further, the organic material layer may be manufactured to have the smaller number of layers by using various polymer materials and by not the deposition method but the solvent process, for example, a method such as spin coating, dip coating, doctor blading, screen printing, inkjet printing, or a heat transferring method.

It is preferable that the anode material be, in general, a material having a large work function so as to smoothly inject the holes into the organic material layer. Specific examples of the anode material that may be used in the present specification include metal such as vanadium, chrome, copper, zinc, and gold, or an alloy thereof; metal oxides such as zinc oxides, indium oxides, indium tin oxides (ITO), and indium zinc oxides (IZO); a combination of metal and oxides, such as ZnO:Al or $SnO_2$:Sb; conductive polymers such as poly(3-methyl compound), poly[3,4-(ethylene-1,2-dioxy)thiophene] (PEDT), polypyrrole, and polyaniline, and the like, but are not limited thereto.

It is preferable that the cathode material be, in general, a material having a small work function so as to easily inject the electrons into the organic material layer. Specific examples of the cathode material include metal such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material is a material that may receive holes well from the anode at a low voltage, and it is preferable that a HOMO (highest occupied molecular orbital) of the hole injection material be a value between the work function of the anode material and the HOMO of the surrounding organic material layer. Specific examples of the hole injection material include metal porphyrine, oligothiophene, an arylamine-based organic material, a hexanitrile-hexaazatriphenylene-based organic material, a quinacridone-based organic material, a perylene-based organic material, anthraquinone, polyaniline, a polycompound-based conductive polymer, and the like, but are not limited thereto.

The hole transport material is a material that may receive the holes from the anode or the hole injection layer and transport the holes to the light emitting layer, and is preferably a material having large mobility to the holes. Specific examples thereof include an arylamine-based organic material, a conductive polymer, a block copolymer in which a conjugate portion and a non-conjugate portion are present together, and the like, but are not limited thereto.

The light emitting material is a material that may receive the holes and the electrons from the hole transport layer and the electron transport layer, respectively, and bond the holes and the electrons to emit light in a visible ray region, and is preferably a material having good quantum efficiency to fluorescence or phosphorescence.

Specific examples thereof include an 8-hydroxy-quinoline aluminum complex ($Alq_3$); a carbazole-based compound; a dimerized styryl compound; BAlq; a 10-hydroxybenzoquinoline-metal compound; benzoxazolee, benzthiazole and benzimidazole-based compounds; a poly(p-phenylenevinylene) (PPV)-based polymer; a spiro compound; polyfluorene; lubrene, and the like, but are not limited thereto.

The electron transport material is a material that may receive well the electrons from the cathode and transport the electrons to the light emitting layer, and is preferably a material having large mobility to the electrons. Specific examples thereof include an 8-hydroxyquinoline Al complex; a complex including $Alq_3$; an organic radical compound; a hydroxyflavone-metal complex, and the like, but are not limited thereto.

The organic electronic device according to the present specification may be a top emission type, a bottom emission type, or a dual emission type according to the used material.

The organic electronic device according to the present specification may be an organic light emitting device.

Figure 2:
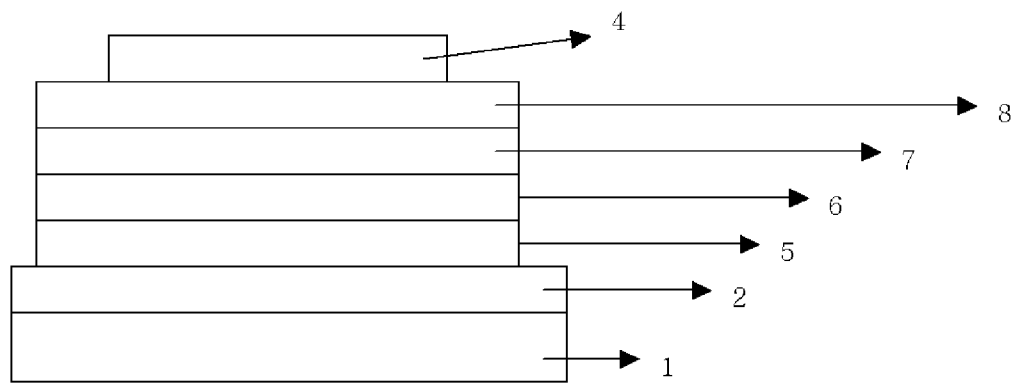
FIG. 2 illustrates an example of an organic electronic device including a substrate 1, an anode 2, a hole injection layer 5, a hole transport layer 6, a light emitting layer 7, an electron transport layer 8, and a cathode 4.

For example, the structure of the organic light emitting device of the present specification may have a structure shown in FIGS. 1 and 2, but is not limited thereto.

FIG. 1 illustrates a structure of an organic electronic device in which an anode 2, a light emitting layer 3, and a cathode 4 are sequentially laminated on a substrate 1. In the aforementioned structure, the compound may be included in the light emitting layer 3.

FIG. 2 illustrates a structure of an organic light emitting device in which an anode 2, a hole injection layer 5, a hole transport layer 6, a light emitting layer 7, an electron transport layer 8, and a cathode 4 are sequentially laminated on a substrate 1. In the aforementioned structure, the compound may be included in the hole injection layer 5, the hole transport layer 6, the light emitting layer 7, or the electron transport layer 8.

The compound according to the exemplary embodiment of the present application may be used in the organic material layer of the organic light emitting device, and more specifically, the electron transport layer or the light emitting layer.

An organic solar cell according to the present specification may have a structure including a first electrode, a second electrode, and an organic material layer disposed therebetween, and may include a hole transport layer, a light active layer, and a electron transport layer as the organic material layer. The compound according to the exemplary embodiment of the present application may be used in the organic material layer of the organic solar cell, and more specifically, the electron transport layer.

An organic photoconductor according to the present specification may include a conductive base material, an electric charge transport layer including an electron transport material, and an electric charge generation layer. The compound according to the exemplary embodiment of the present application may be used in the electric charge transport layer of the organic photoconductor.

An organic transistor according to the present specification may include a first electrode, a second electrode, a hole injection layer, an organic thin film layer, an electron injection layer, an electron transport layer, and the like. The compound according to the exemplary embodiment of the present application may be used in the electron transport layer of the organic transistor.

MODE FOR INVENTION

The method of manufacturing the compound of Chemical Formula 1 and the manufacturing of the organic electronic device using the same will be described in detail in the following Examples. However, the following Examples are set forth to illustrate the present specification, but the scope of the present specification is not limited thereto.

EXAMPLE

Synthetic Example 1 hydrofuran (200 mL), and cooling was performed to 0° C. 3.0M $CH_3MgBr$ (55 ml, 164.5 mmol) was added thereto for 30 minutes, and agitation was performed at normal temperature for 16 hours. After cooling to 0° C., the reaction was quenched by $NH_4Cl$. The organic layer was separated and then concentrated to obtain Structural Formula B.

3) Manufacturing of Structural Formula C

After Structural Formula B obtained in the aforementioned reaction was dissolved in acetic acid (200 mL), 1 g of concentrated $H_2SO_4$ was added thereto. After reflux for 96 hours, cooling to normal temperature was performed. $H_2O$ (500 ml) was added to generate a solid. After filtration, the solid was purified by the chromatography to obtain Structural Formula C (6.3 g, yield 30%).

MS: $[M+H]^+=382$

Figure 3:
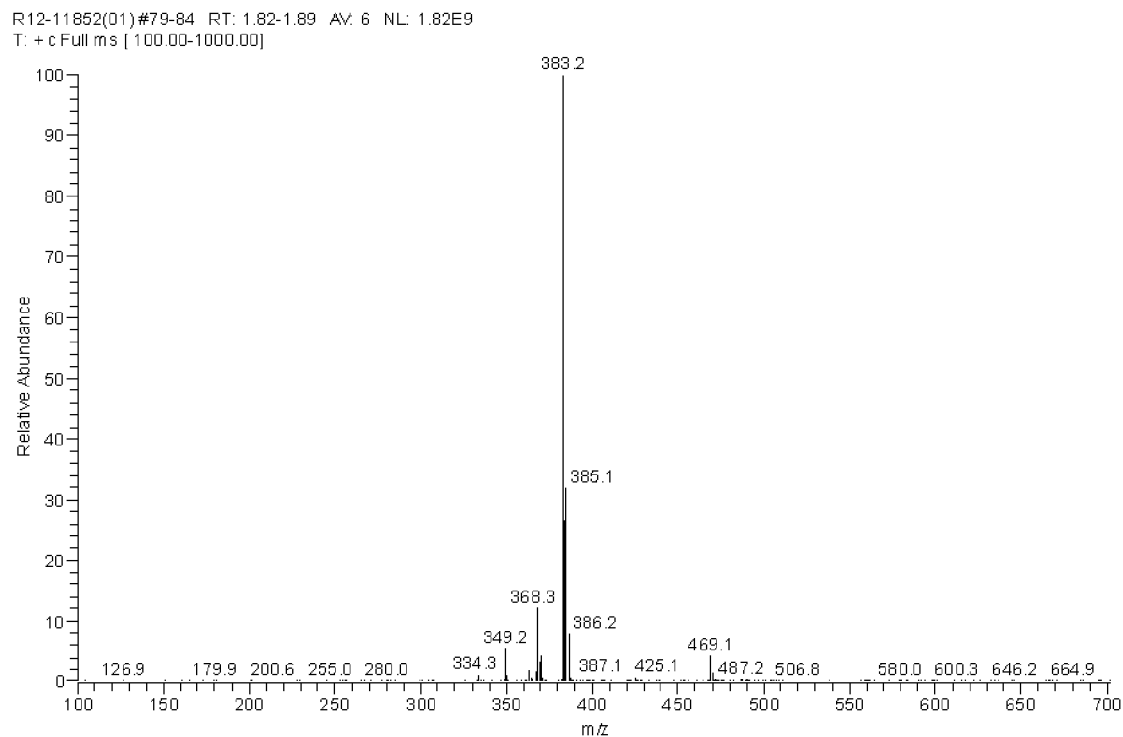
FIG. 3 is an NMR graph of Chemical Formula C of Synthetic Example 1 according to an exemplary embodiment of the present specification.

The NMR graph of Structural Formula C is illustrated in FIG. 3.

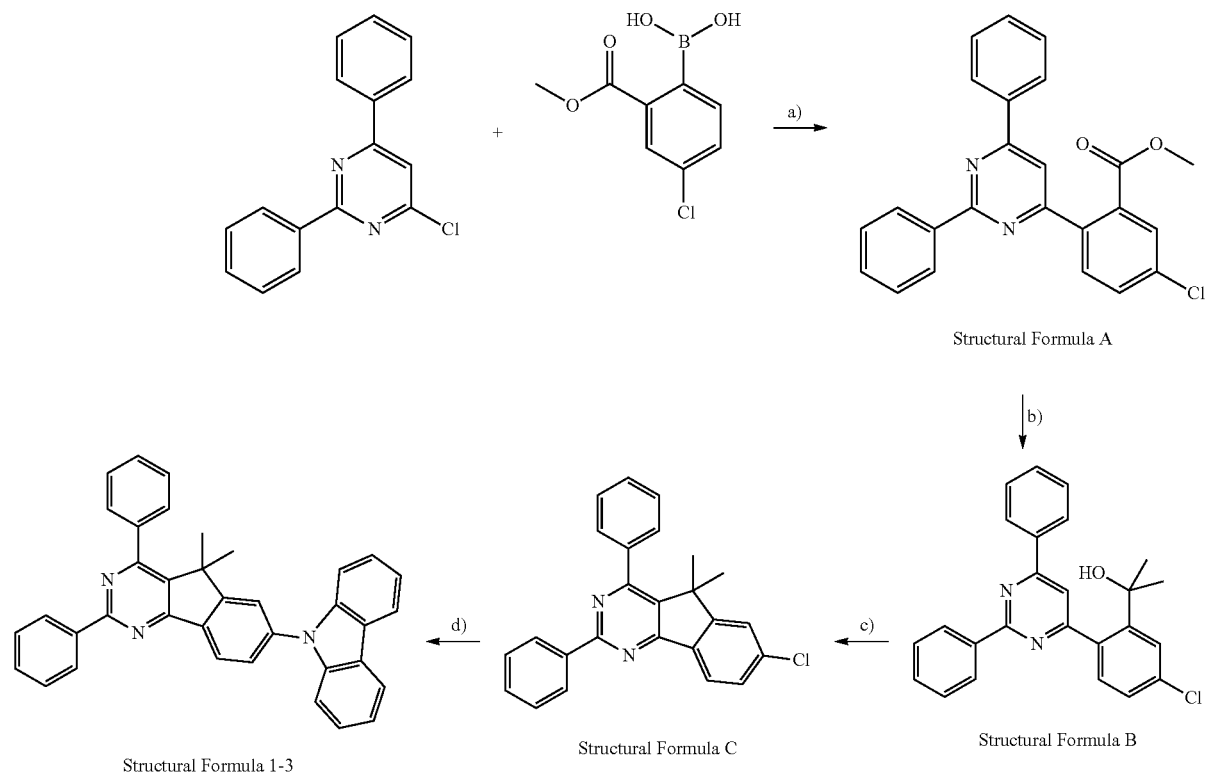

Structural Formula 1-3 a) Pd(ph$_3$)$_4$, b) CH$_3$MgBr, c) H$_2$SO$_4$, AcOH, d) CH$_3$MgBr, e) Pd(p-tBu$_3$)$_2$, carbazole 1) Manufacturing of Structural Formula A 4-chloro-2,6-diphenyl pyrimidine (30.4 g, 114 mmol), 2-(methoxy carbonyl)-4-chlorophenyl boronic acid (25.7 g, 120 mmol), and $K_2CO_3$ (45.6 g, 329 mmol) were refluxed for 12 hours after tetrahydrofuran (THF, 300 mL), $H_2O$ (100 ml), and Pd(PPh$_3$)$_4$ (3.95 g, 3.42 mmol) were added thereto. After cooling to normal temperature, the water layer was removed. After $MgSO_4$ was added to the organic layer, filtration was performed. After concentration, purification was performed by the column chromatography to obtain Structural Formula A (24.2 g, yield 53%).

2) Manufacturing of Structural Formula B

Structural Formula A (22.0 g, 50.5 mmol) obtained in the aforementioned reaction was dissolved in anhydrous tetra- Synthesis of Chemical Formula 1-3

Structural Formula C (5.0 g, 13.1 mmol), carbazole (2.3 g, 13.7 mmol), NaOtBu (1.65 g, 17.0 mmol), Pd(p-tBu$_3$)$_2$ (65 mg, 0.13 mmol), and xylene (50 mL) were mixed, refluxing was performed for 24 hours, and cooled to normal temperature. After filtration, the filtrate was distilled under reduced pressure. The generated solid was purified by the chromatography to obtain Chemical Formula 1-3 (4.96 g, yield 74%).

MS: $[M+H]^+=514$

Figure 4:
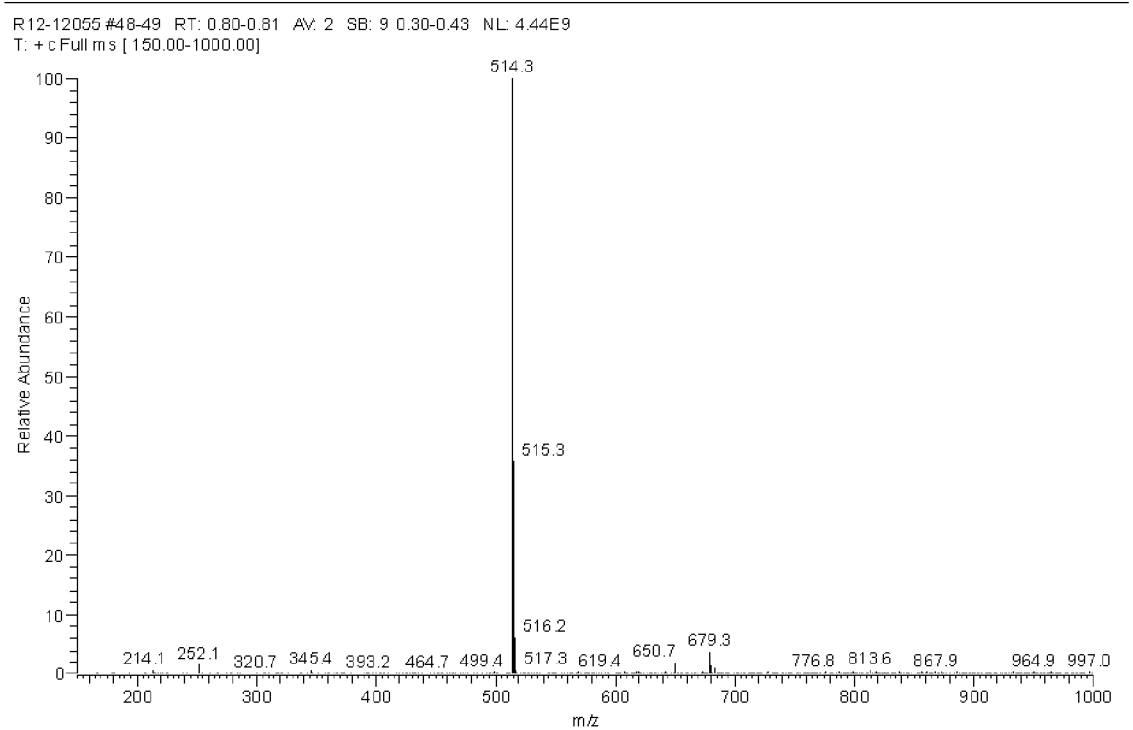
FIG. 4 is an NMR graph of Chemical Formula 1-3 of Synthetic Example 1 according to the exemplary embodiment of the present specification.

The NMR graph of Chemical Formula 1-3 is illustrated in FIG. 4.

Synthetic Example 2

Synthesis of Chemical Formula 1-7

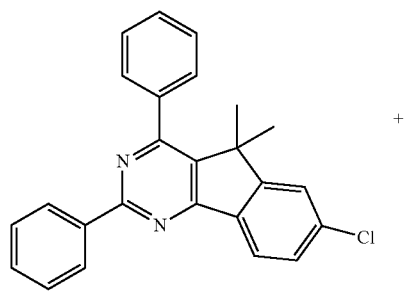

Structural Formula C

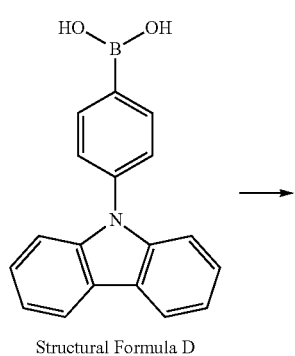

Structural Formula D

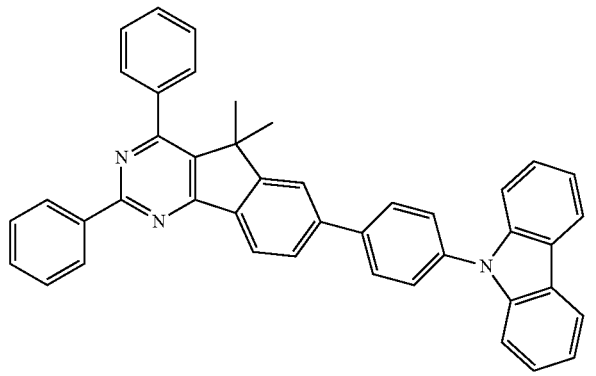

Chemical Formula 1-7

Structural Formula C (10.0 g, 26.1 mmol), Structural Formula D (8.2 g, 28.7 mmol), $K_3PO_4 \cdot H_2O$ (16.6 g, 78.3 mmol), $Pd(p\text{-}tBu_3)_2$ (0.13 g, 0.26 mmol), 1,4-dioxane (100 mL), and $H_2O$ (30 ml) were mixed, refluxing was performed for 24 hours, and cooled to normal temperature. After the water layer was removed, the organic layer was distilled under reduced pressure. The generated solid was purified by the chromatography to obtain Chemical Formula 1-7 (8.0 g, yield 52%).

MS: $[M+H]^+=590$

Synthetic Example 3

Synthesis of Chemical Formula 1-11

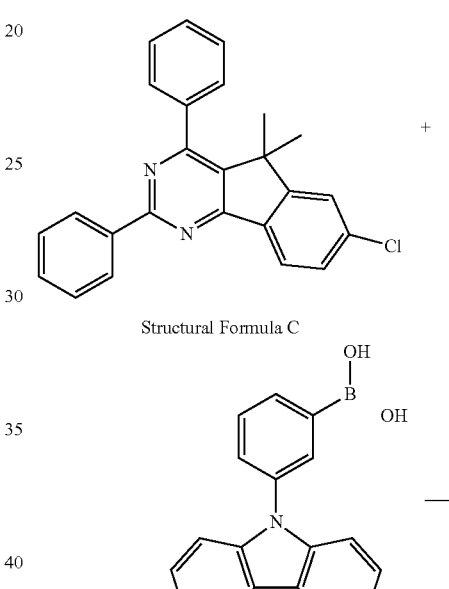

Structural Formula C

Structural Formula E

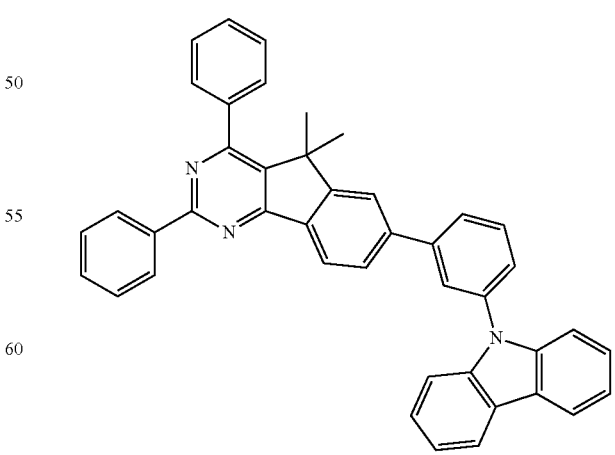

Chemical Formula 1-11

Structural Formula C (10.0 g, 26.1 mmol), Structural Formula E (8.2 g, 28.7 mmol), K$_3$PO$_4$.H$_2$O (16.6 g, 78.3 mmol), Pd(p-tBu$_3$)$_2$ (0.13 g, 0.26 mmol), 1,4-dioxane (100 mL), and H$_2$O (30 ml) were mixed, refluxing was performed for 24 hours, and cooled to normal temperature. After the water layer was removed, the organic layer was distilled under reduced pressure. The generated solid was purified by the chromatography to obtain Chemical Formula 1-11 (5.4 g, yield 35%).

MS: [M+H]$^+$=590

Structural Formula C (15.0 g, 39.2 mmol), Structural Formula F (9.8 g, 43.1 mmol), K$_3$PO$_4$.H$_2$O (24.9 g, 118 mmol), Pd(p-tBu$_3$)$_2$ (0.20 g, 0.39 mmol), 1,4-dioxane (100 mL), and H$_2$O (30 ml) were mixed, refluxing was performed for 24 hours, and cooled to normal temperature. After the water layer was removed, the organic layer was distilled under reduced pressure. The generated solid was purified by the chromatography to obtain Chemical Formula 1-15 (7.9 g, yield 38%).

MS: [M+H]$^+$=531

Synthetic Example 4

Synthesis of Chemical Formula 1-15

Synthetic Example 5

Synthesis of Chemical Formula 1-55

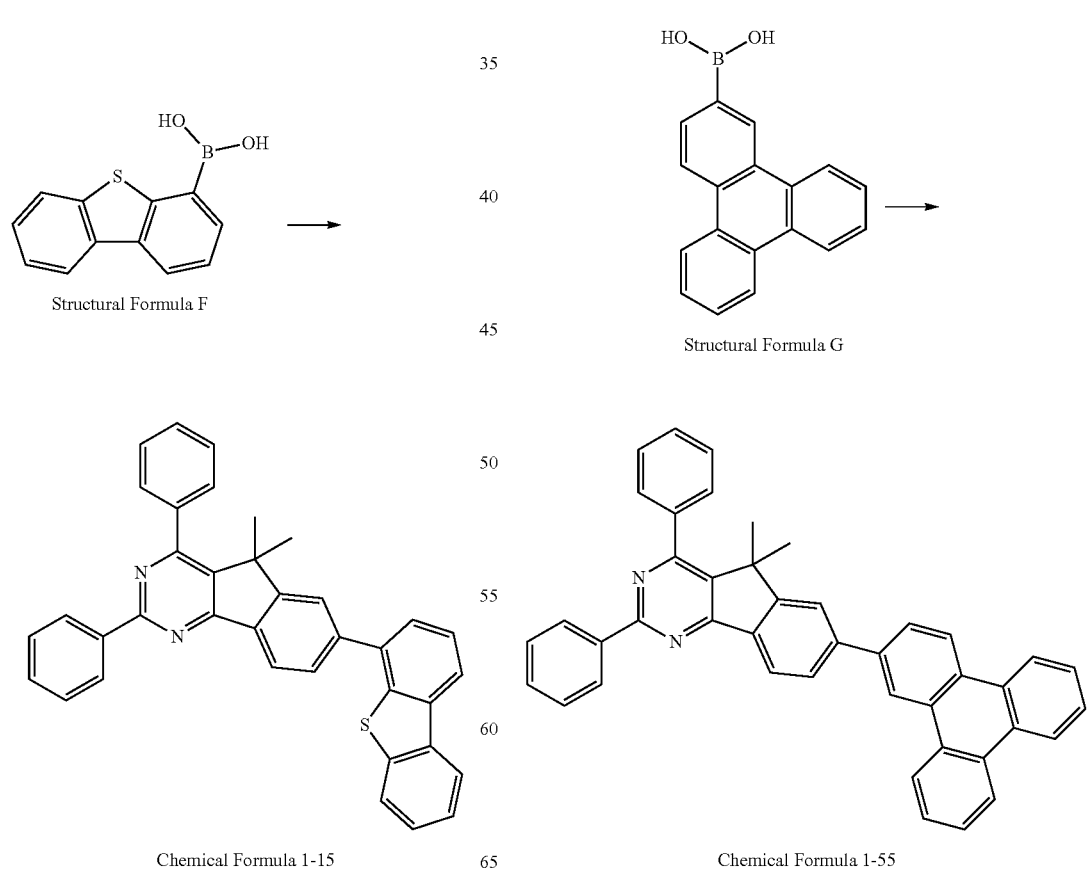

Structural Formula C (12.0 g, 31.3 mmol), Structural Formula G (9.4 g, 34.4 mmol), K$_3$PO$_4$.H$_2$O (20.0 g, 94.4 mmol), Pd(p-tBu$_3$)$_2$ (0.16 g, 0.31 mmol), 1,4-dioxane (100 mL), and H$_2$O (30 ml) were mixed, refluxing was performed for 24 hours, and cooled to normal temperature. After the water layer was removed, the organic layer was distilled under reduced pressure. The generated solid was purified by the chromatography to obtain Chemical Formula 1-55 (4.5 g, yield 25%).

MS: [M+H]$^+$=575

Example 1

A glass substrate on which a thin film of ITO (indium tin oxide) was applied in a thickness of 500 Å was put into distilled water having the detergent dissolved therein and washed by the ultrasonic wave. In this case, the product manufactured by Fisher Co. was used as the detergent, and distilled water, which had been twice filtered by the filter manufactured by Millipore Co., was used as the distilled water. The ITO was washed for 30 minutes, and then washing with ultrasonic waves was repeated twice for 10 minutes by distilled water. After washing with distilled water was finished, washing with ultrasonic waves was performed by solvents such as isopropyl alcohol, acetone, and methanol, and the resultant product was dried and transported to the plasma washing machine. Further, the substrate was washed by using oxygen plasma for 5 minutes, and then transported to the vacuum deposition machine.

Hexanitrile hexaazatriphenylene (HAT) of the following Chemical Formula was thermally deposited under vacuum in a thicknesses of 500 Å on the ITO transparent electrode thus prepared to form a hole injection layer.

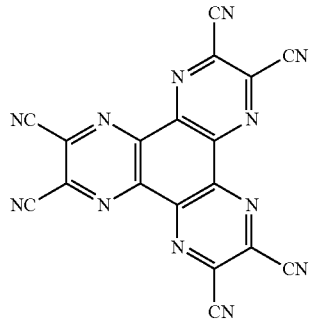

[HAT]

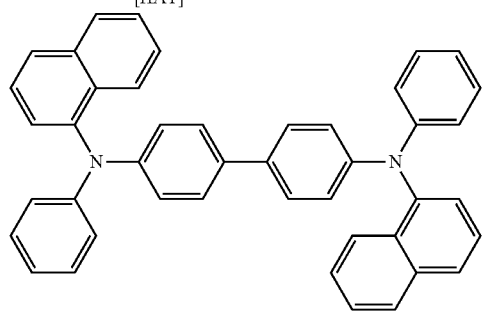

[NPB]

4,4'-bis[N-(1-naphthyl)-N-phenylamino]biphenyl (NPB) (250 Å), hexanitrile hexaazatriphenylene (HAT) (50 Å) and 4,4'-bis[N-(1-naphthyl)-N-phenylamino]biphenyl (NPB) (400 Å) of the aforementioned Chemical Formulas were sequentially deposited under vacuum on the hole injection layer to form a hole transport layer.

Subsequently, the compound of Chemical Formula 1-3 manufactured in Synthetic Example 1 and a dopant compound GD as illustrated below were deposited under vacuum at a weight ratio of 10:1 in a film thickness of 300 Å on the hole transport layer to form a light emitting layer.

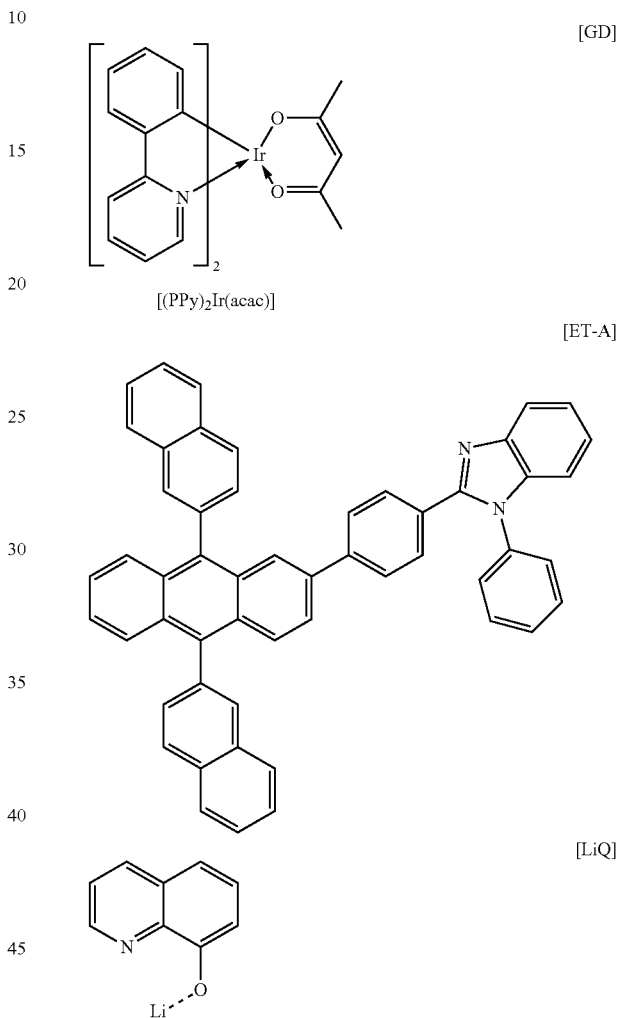

The compound of Chemical Formula ET-A as the electron transport layer material and the aforementioned Chemical Formula LiQ (lithium quinalate) were deposited under vacuum at a weight ratio of 1:1 on the light emitting layer to form an electron injection and transport layer in a thickness of 300 Å.

Lithium fluoride (LiF) in a thickness of 15 Å and aluminum in a thickness of 1,000 Å were sequentially deposited on the electron injection and transport layer to form a cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at 2×10$^{-7}$ to 5×10$^{-8}$ torr to manufacture an organic light emitting device.

Example 2

An organic light emitting device was manufactured by the same method as Example 1, except that the compound of the following Chemical Formula 1-7 was used instead of the compound of Chemical Formula 1-3 in Example 1.

Example 3

An organic light emitting device was manufactured by the same method as Example 1, except that the compound of the following Chemical Formula 1-11 was used instead of the compound of Chemical Formula 1-3 in Example 1.

Example 4

An organic light emitting device was manufactured by the same method as Example 1, except that the compound of the following Chemical Formula 1-15 was used instead of the compound of Chemical Formula 1-3 in Example 1.

Example 5

An organic light emitting device was manufactured by the same method as Example 1, except that the compound of the following Chemical Formula 1-55 was used instead of the compound of Chemical Formula 1-3 in Example 1.

Comparative Example 1

An organic light emitting device was manufactured by the same method as Example 1, except that the compound of the following Chemical Formula GH-A was used instead of the compound of Chemical Formula 1-3 in Example 1.

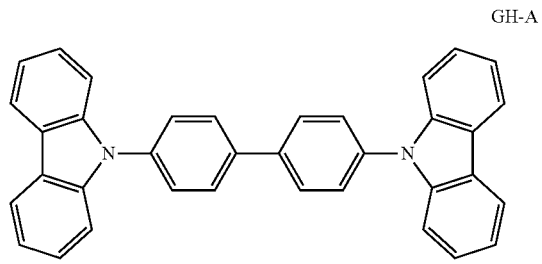 [SMILES: c1ccc2c(c1)c1ccccc1n2-c1ccc(-c2ccc(-n3c4ccccc4c4ccccc43)cc2)cc1]

GH-A

Experimental Example 1

When the current (10 mA/cm$^2$) was applied to the organic light emitting devices manufactured in Examples 1 to 5 and Comparative Example 1, the results of Table 1 were obtained.

TABLE 1

| | Compound | Voltage (V) | Efficiency (cd/A) |
|---|---|---|---|
| Experimental Example 1 | Chemical Formula 1-3 | 3.50 | 67.10 |
| Experimental Example 2 | Chemical Formula 1-7 | 3.70 | 65.57 |
| Experimental Example 3 | Chemical Formula 1-11 | 3.93 | 62.32 |
| Experimental Example 4 | Chemical Formula 1-15 | 4.10 | 57.53 |
| Experimental Example 5 | Chemical Formula 1-55 | 4.37 | 61.38 |
| Comparative Example 1 | GH-A | 6.12 | 15.26 |

From the results of Table 1, it can be seen that the novel compound according to the present specification may be used as the material of the light emitting layer of the organic electronic device including the organic light emitting device, and the organic electronic device including the organic light emitting device using the same has excellent characteristics in view of efficiency, driving voltage, stability and the like. Particularly, the compound may reduce a driving voltage and introduce an increase in efficiency to improve power consumption.

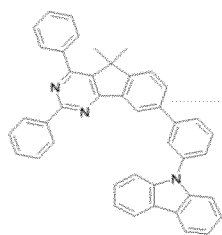 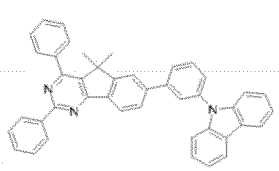 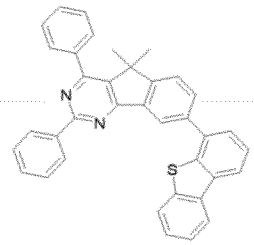

[Chemical Formula 1-18]　　[Chemical Formula 1-19]　　[Chemical Formula 1-22]　　[Chemical Formula 1-23]
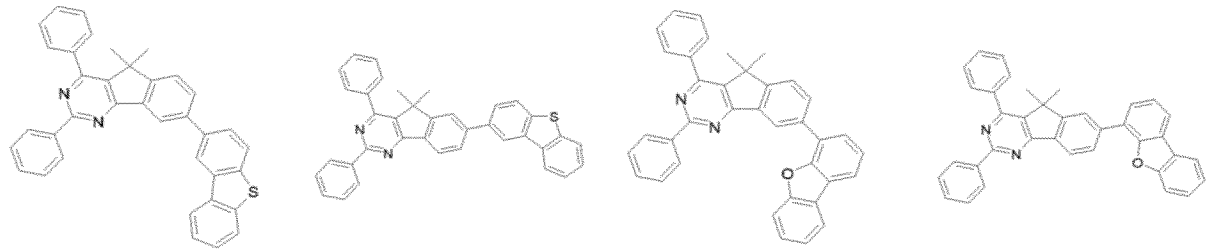
[Chemical Formula 1-26]　　[Chemical Formula 1-27]　　[Chemical Formula 1-30]　　[Chemical Formula 1-31]
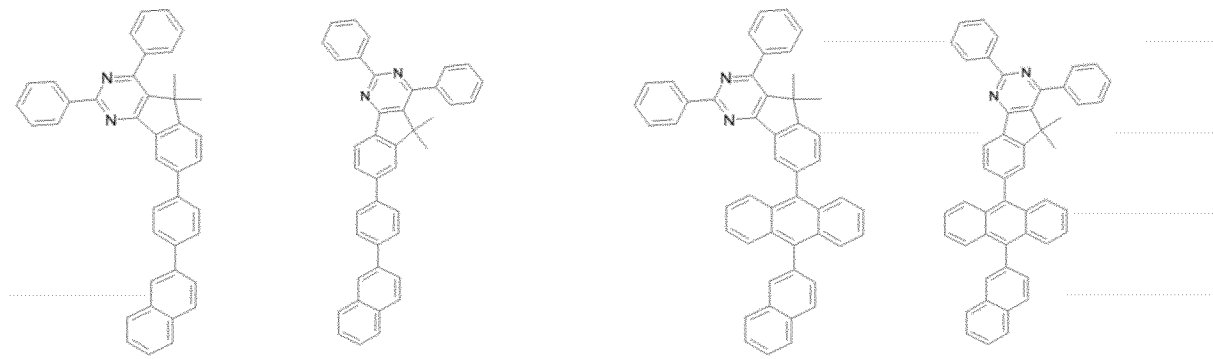
[Chemical Formula 1-34]　　[Chemical Formula 1-35]　　[Chemical Formula 1-38]　　[Chemical Formula 1-39]
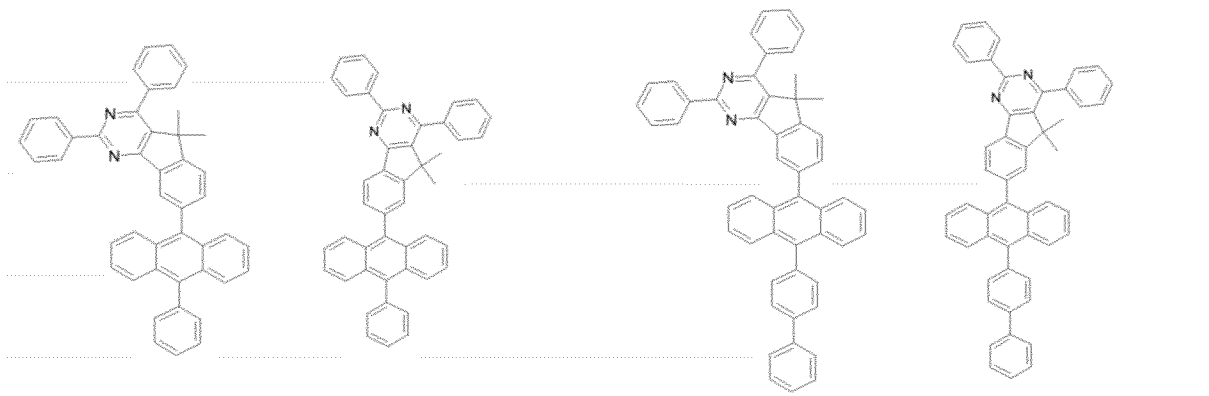
[Chemical Formula 1-42]　　[Chemical Formula 1-43]　　[Chemical Formula 1-46]　　[Chemical Formula 1-47]
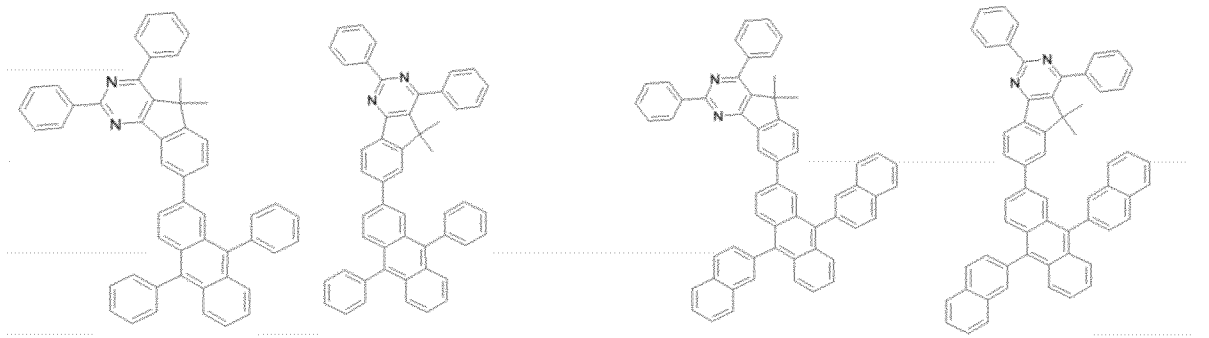

[Chemical Formula 1-50]  [Chemical Formula 1-51]  [Chemical Formula 1-54]  [Chemical Formula 1-55]
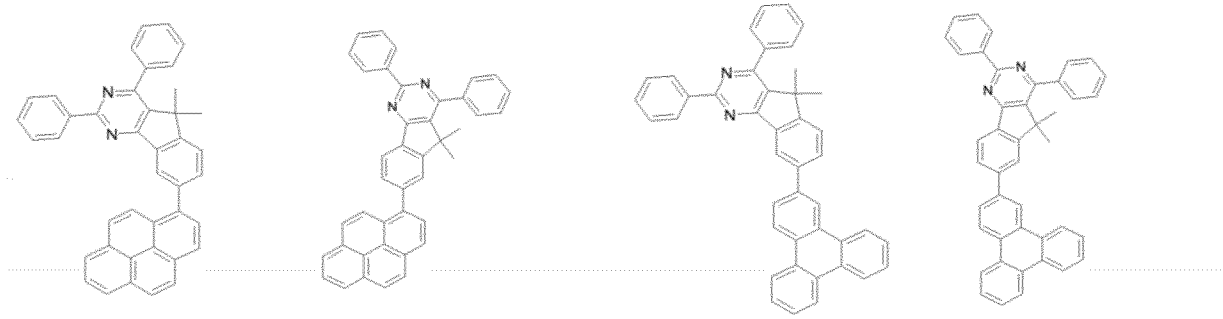
[Chemical Formula 1-58]  [Chemical Formula 1-59]  [Chemical Formula 1-61]  [Chemical Formula 1-62]
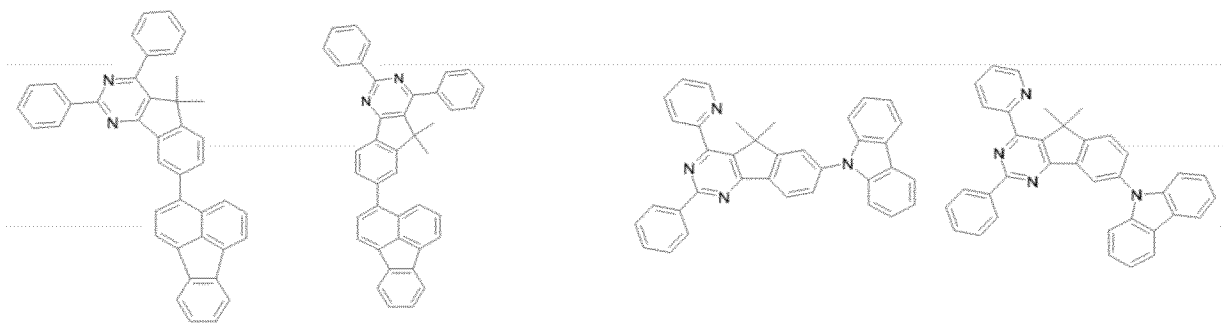
[Chemical Formula 1-63]  [Chemical Formula 1-64]  [Chemical Formula 1-65]  [Chemical Formula 1-66]
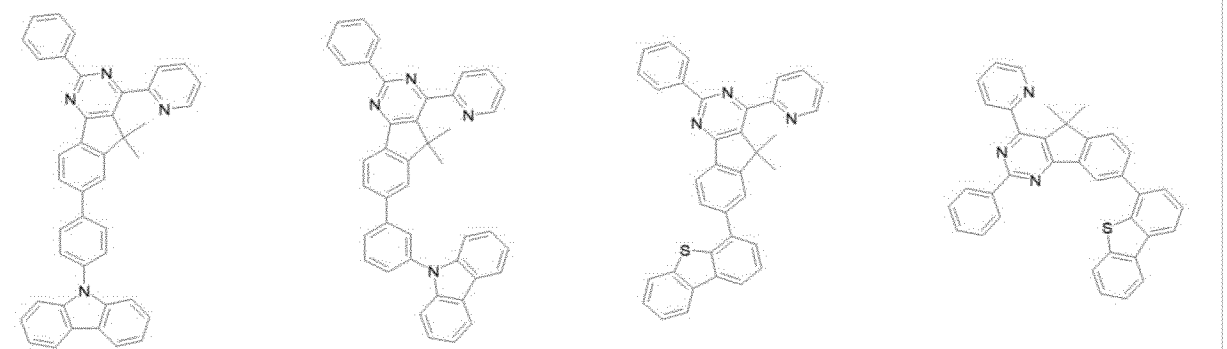
[Chemical Formula 1-67]  [Chemical Formula 1-68]
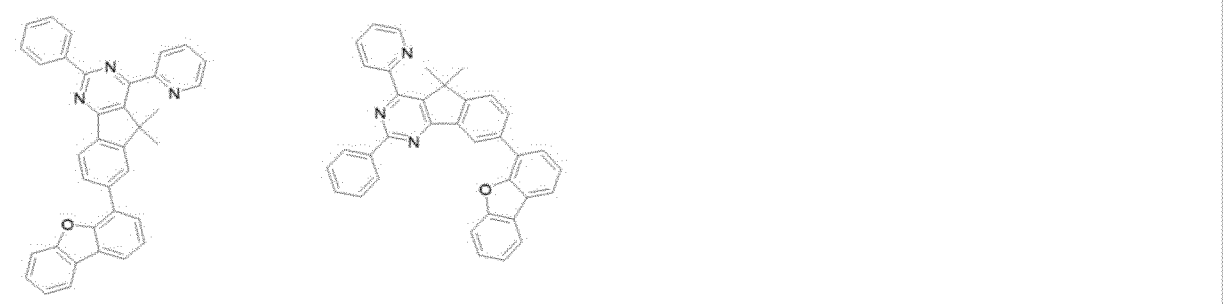

The invention claimed is:

1. An organic electronic device comprising:
a first electrode; a second electrode; and
one or more organic material layers disposed between the first electrode and the second electrode,
wherein the organic material layers include a light emitting layer,
wherein the light emitting layer includes the compound represented by the following Chemical Formula 1:

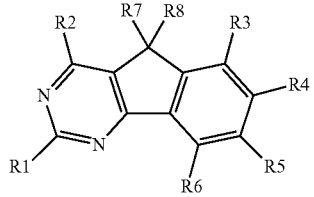

[Chemical Formula 1]

wherein
at least one of R1 to R6 is -L-A, and the rest are the same as or different from each other, and are each independently hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, and S atoms, L is a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group, A is an unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenalenyl group; a substituted or unsubstituted naphthacenyl group; a substituted or unsubstituted pentacenyl group; a substituted or unsubstituted phenanthrenyl group; a substituted or unsubstituted pyrenyl group; a substituted or unsubstituted triphenylenyl group; a substituted or unsubstituted fluoranthenyl group; a substituted or unsubstituted perylenyl group; a substituted or unsubstituted chrysenyl group; a substituted or unsubstituted carbazole group; a substituted or unsubstituted dibenzothiophene group; or a substituted or unsubstituted dibenzofuran group, when the R2 is -L-A, A is an unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenalenyl group; a substituted or unsubstituted naphthacenyl group; a substituted or unsubstituted pentacenyl group; a substituted or unsubstituted perylenyl group; a substituted or unsubstituted chrysenyl group; a substituted or unsubstituted carbazole group; or a substituted or unsubstituted dibenzofuran group, and R7 and R8 are the same as or different from each other, and are each independently a halogen group; a nitrile group; a nitro group; a hydroxy group; or an unsubstituted alkyl group.

2. The organic electronic device of claim 1, wherein at least one of R1 to R6 is a substituted or unsubstituted carbazole group, a substituted or unsubstituted dibenzothiophene group, or a substituted or unsubstituted dibenzofuran group.

3. The organic electronic device of claim 1, wherein at least one of R3 to R6 includes any one of a substituted or unsubstituted carbazole group, a substituted or unsubstituted dibenzothiophene group, and a substituted or unsubstituted dibenzofuran group.

4. The organic electronic device of claim 1, wherein R1 and R2 are each independently a substituted or unsubstituted aryl group.

5. The organic electronic device of claim 1, wherein R7 and R8 are the same as or different from each other, and are each independently an unsubstituted alkyl group.

6. The organic electronic device of claim 1, wherein:

R1 and R2 are each independently a phenyl group, a biphenyl group, a tolyl group, a naphthyl group, a pyridyl group, a pyrimidyl group, a pyrazinyl group, or a fluorenyl group;

R3 to R6 are each independently hydrogen, heavy hydrogen, a halogen group, a nitrile group, a nitro group, a hydroxy group, a substituted or unsubstituted alkyl group, or -L-A; and at least one of R3 to R6 is -L-A.

7. The compound of claim 1, wherein the compound of Chemical Formula 1 has any one of the following Chemical Formulas:

[Chemical Formula 1-2]

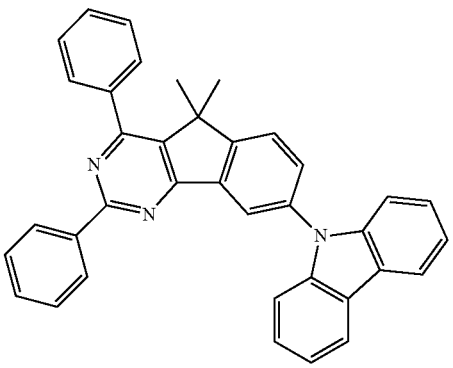

[Chemical Formula 1-3]

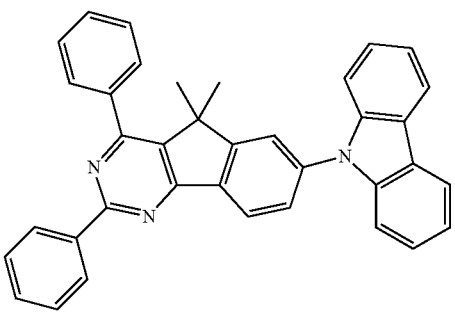

[Chemical Formula 1-6]

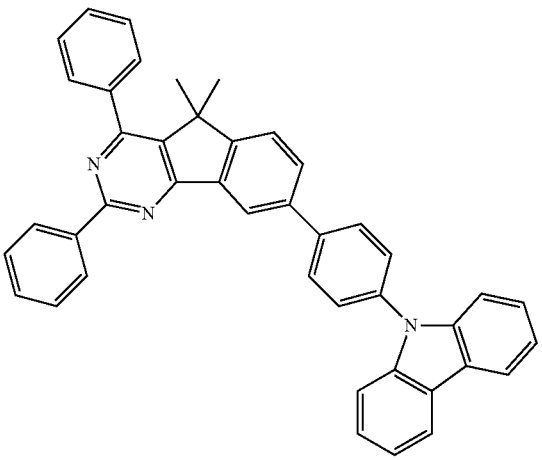

[Chemical Formula 1-7]

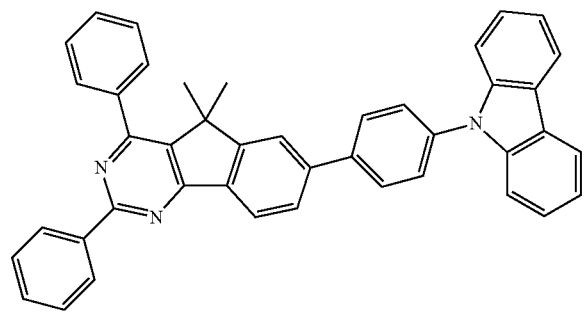

[Chemical Formula 1-10]
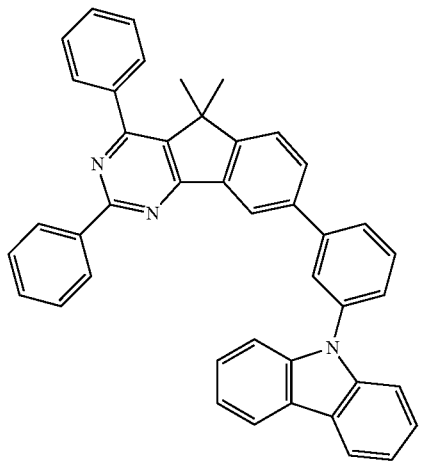
[Chemical Formula 1-11]
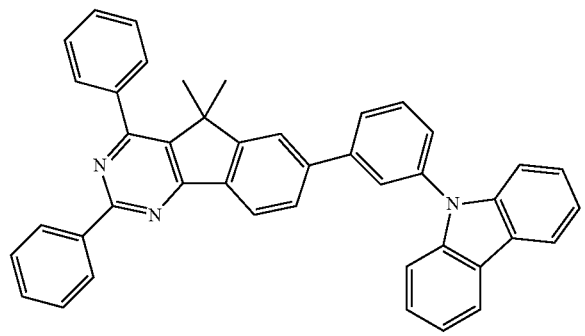
[Chemical Formula 1-14]
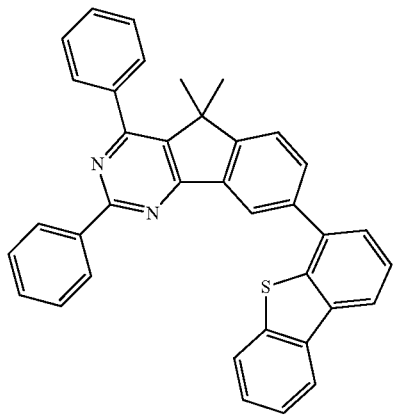
[Chemical Formula 1-15]
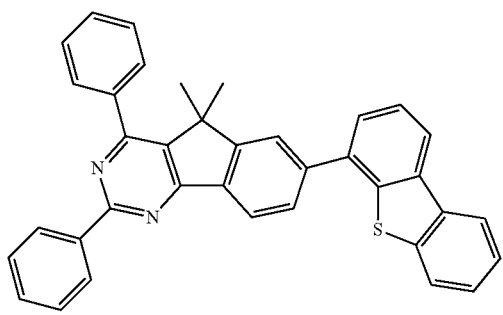
[Chemical Formula 1-18]
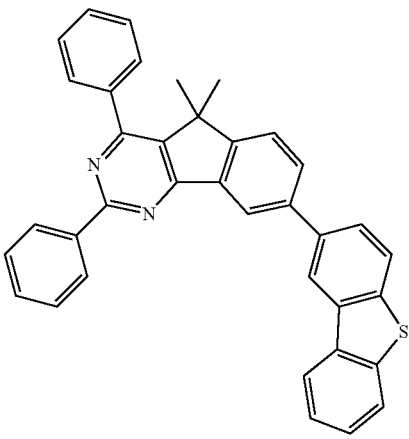
[Chemical Formula 1-19]
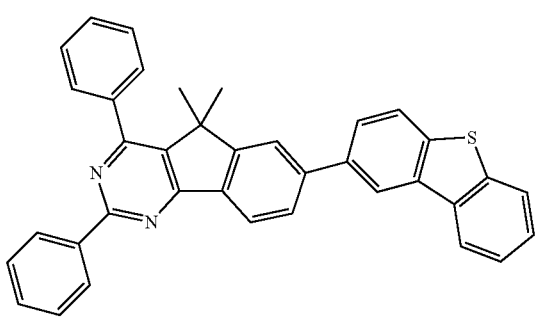
[Chemical Formula 1-22]
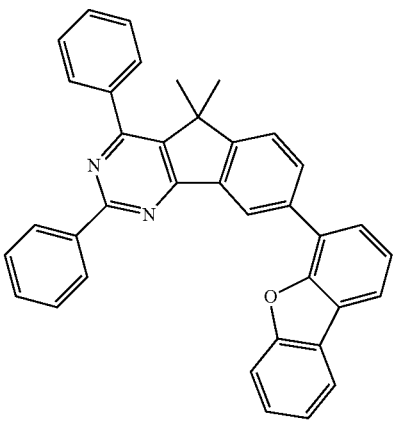
[Chemical Formula 1-23]
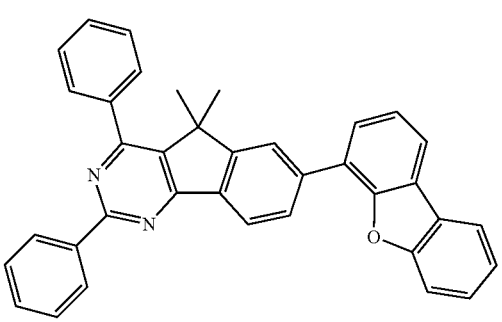

[Chemical Formula 1-26]
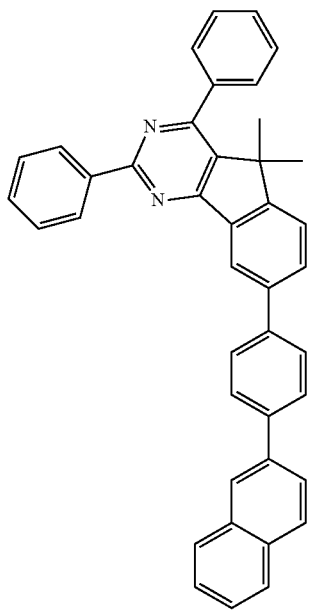
[Chemical Formula 1-30]
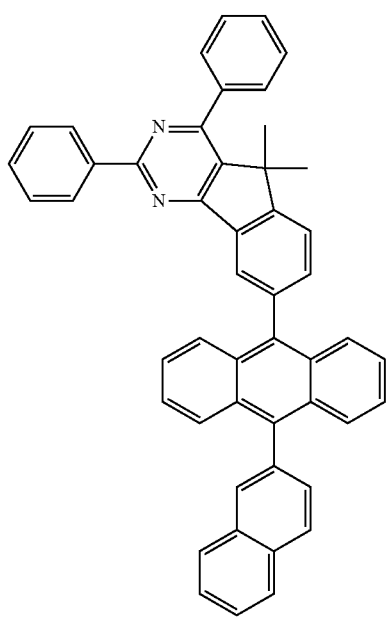
[Chemical Formula 1-27]
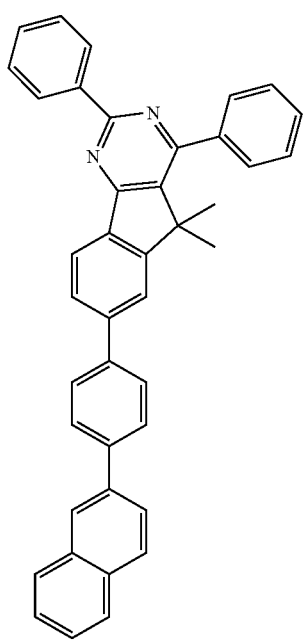
[Chemical Formula 1-31]
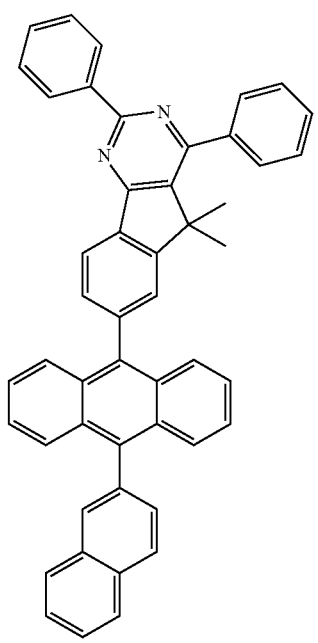

[Chemical Formula 1-34]
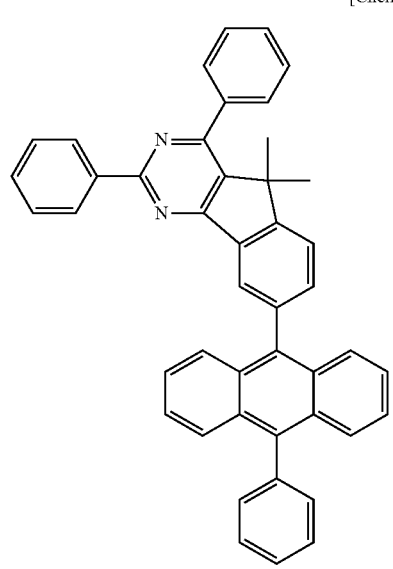
[Chemical Formula 1-35]
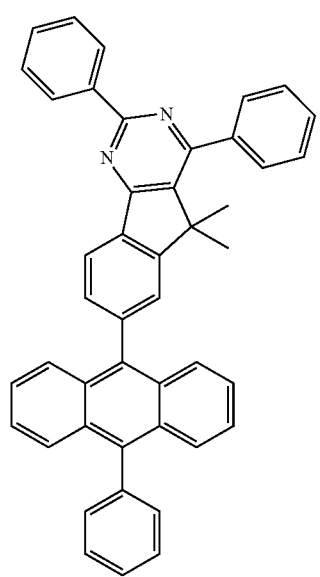
[Chemical Formula 1-38]
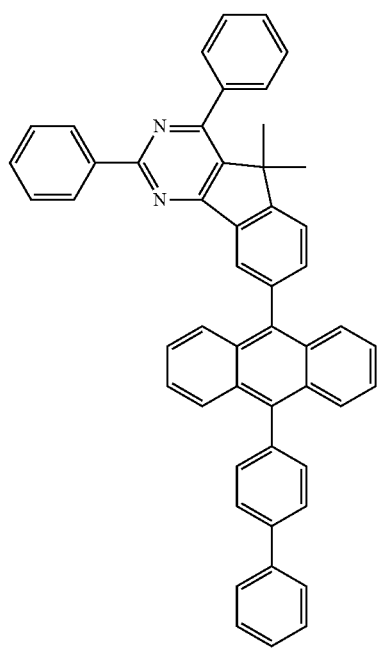
[Chemical Formula 1-39]
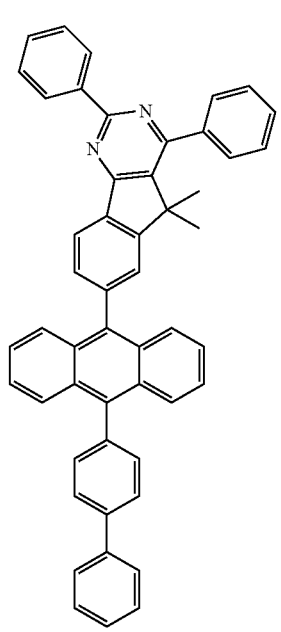

[Chemical Formula 1-42]
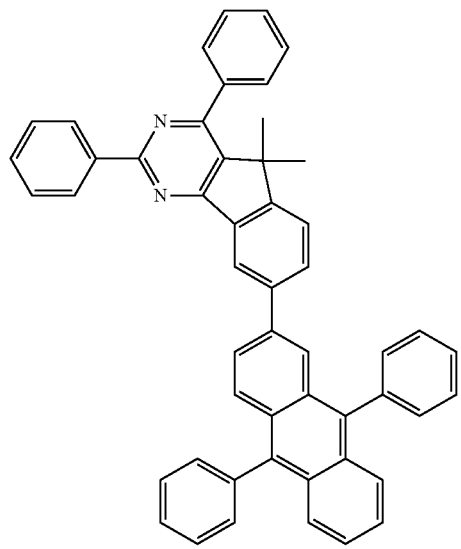
[Chemical Formula 1-46]
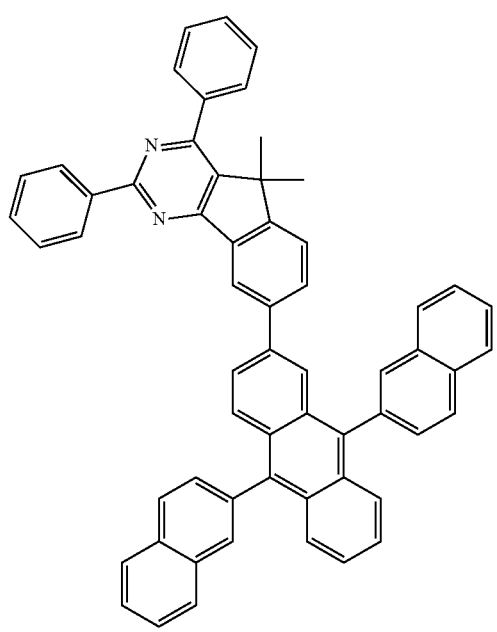
[Chemical Formula 1-43]
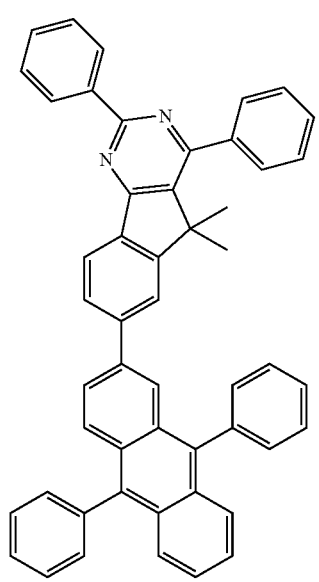
[Chemical Formula 1-47]
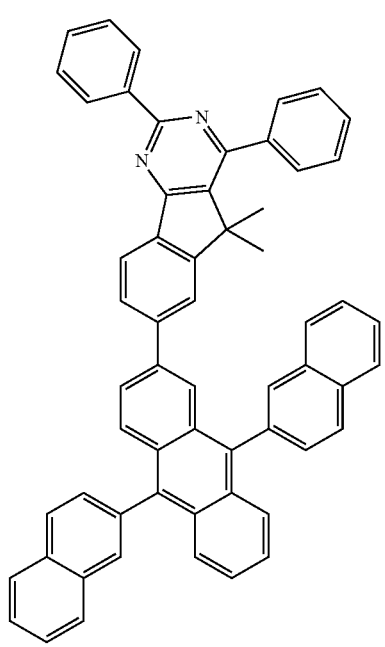

[Chemical Formula 1-50]
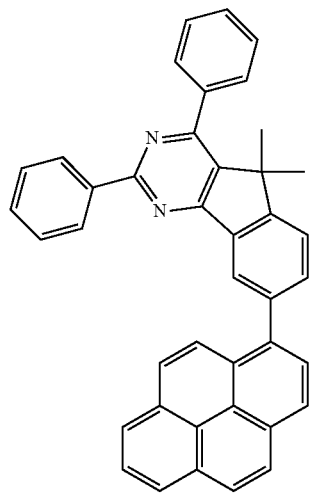
[Chemical Formula 1-51]
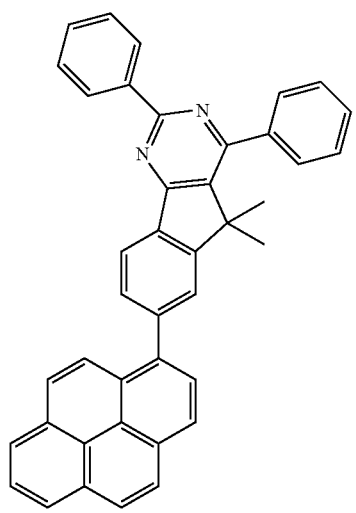
[Chemical Formula 1-54]
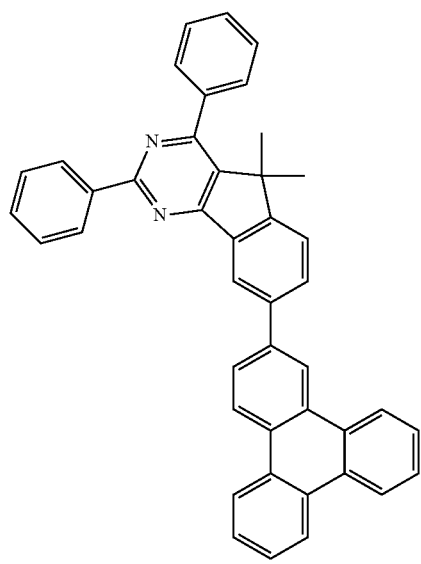
[Chemical Formula 1-55]
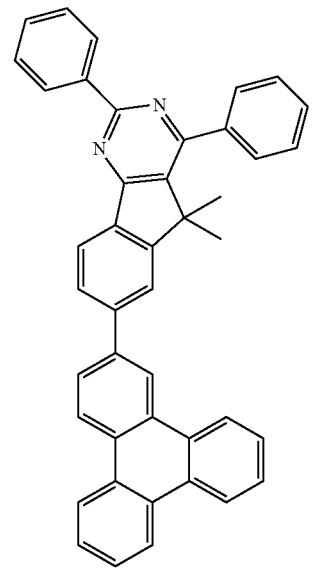
[Chemical Formula 1-58]
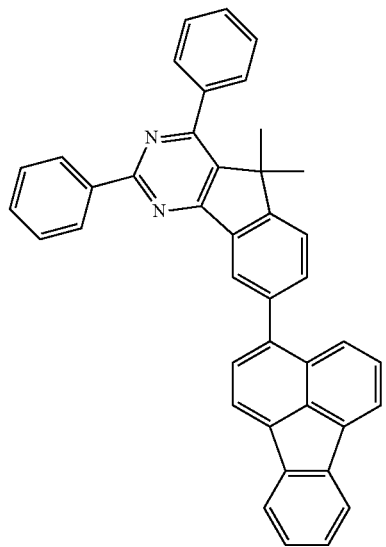

[Chemical Formula 1-59]
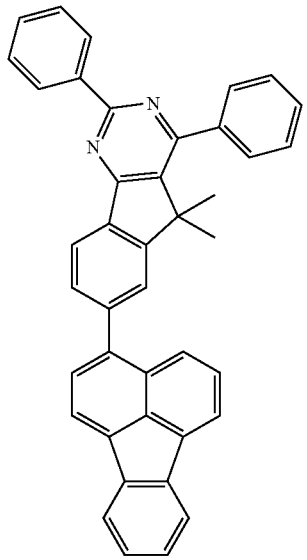
[Chemical Formula 1-63]
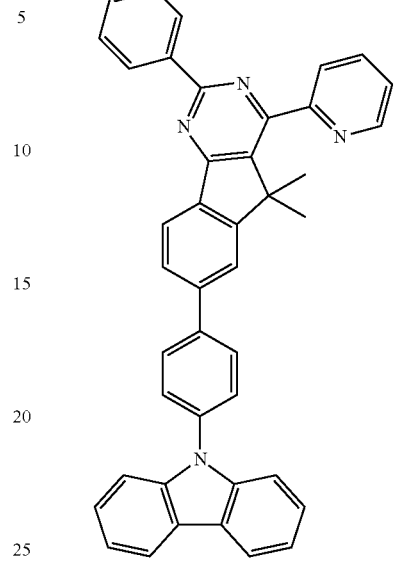
[Chemical Formula 1-61]
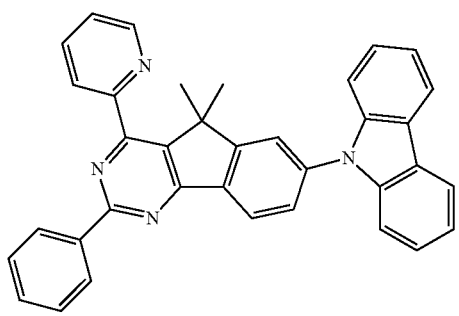
[Chemical Formula 1-62]
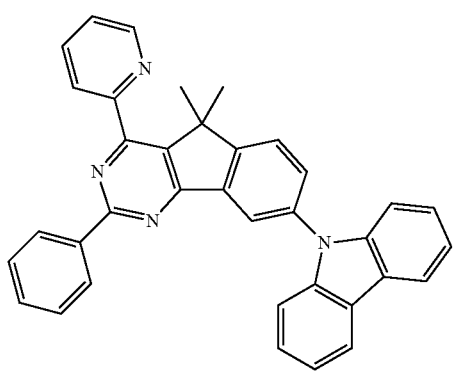
[Chemical Formula 1-64]
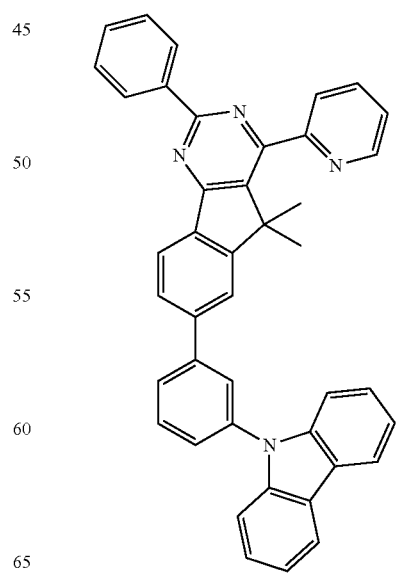

[Chemical Formula 1-65]
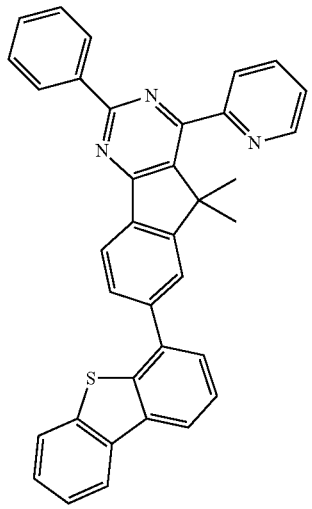
[Chemical Formula 1-66]
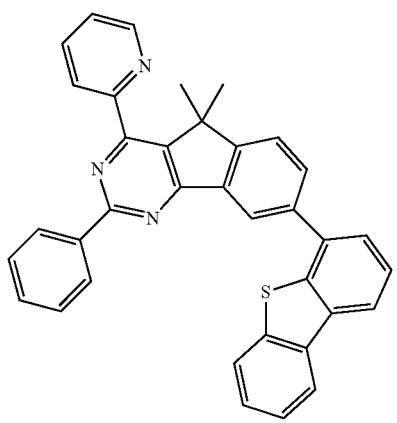
[Chemical Formula 1-67]
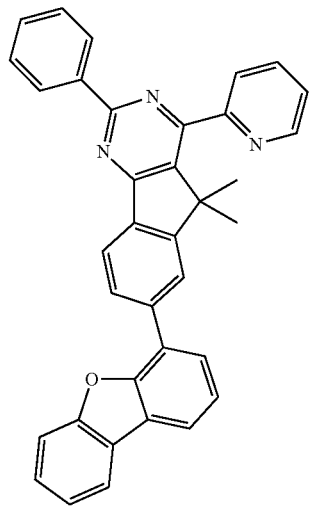
[Chemical Formula 1-68]
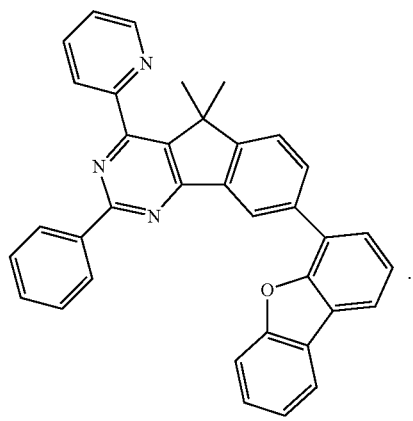
* * * * *

UNITED STATES PATENT AND TRADEMARK OFFICE
CERTIFICATE OF CORRECTION

Page 1 of 4

PATENT NO. : 10,790,453 B2
APPLICATION NO. : 15/495646
DATED : September 29, 2020
INVENTOR(S) : Tae Yoon Park et al.

It is certified that error appears in the above-identified patent and that said Letters Patent is hereby corrected as shown below:

In the Claims

At Column 50, Line 13, to Column 51, Line 37, please replace Claim 1 with the following claim:
1. An organic electronic device comprising:
    a first electrode;
    a second electrode; and
    one or more organic material layers disposed between the first electrode and the second electrode,
    wherein the organic material layers include a light emitting layer,
    wherein the light emitting layer includes the compound of the following Chemical Formula 1:
    [Chemical Formula 1]

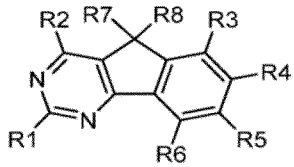

wherein:
    R1 and R2 are the same as or different from each other, and are each independently a substituted or unsubstituted cycloalkyl group; a substituted or unsubstituted aryl group; or a substituted or unsubstituted heterocyclic group including one or more of N, O, and S atoms;
        at least one of R3 to R6 is -L-A, and the rest are the same as or different from each other, and are each independently hydrogen, heavy hydrogen, a halogen group, a nitrile group, a nitro group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or Signed and Sealed this
First Day of December, 2020

Andrei Iancu
*Director of the United States Patent and Trademark Office* a substituted or unsubstituted heterocyclic group including one or more of N, O, and S atoms;

L is a direct bond; an arylene group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group; or a divalent biphenyl group unsubstituted or substituted by one or more substituent groups selected from the group consisting of a halogen group, an alkyl group, an alkenyl group, an alkoxy group, an arylamine group, an aryl group, an arylalkyl group, an arylalkenyl group, a heteroaryl group, a carbazolyl group, a fluorenyl group, and a nitrile group;

A is an unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenalenyl group, a substituted or unsubstituted naphthacenyl group, a substituted or unsubstituted pentacenyl group, a substituted or unsubstituted phenanthrenyl group, a substituted or unsubstituted pyrenyl group, a substituted or unsubstituted triphenylenyl group, a substituted or unsubstituted fluoranthenyl group, a substituted or unsubstituted perylenyl group, a substituted or unsubstituted chrysenyl group, a substituted or unsubstituted carbazole group, a substituted or unsubstituted dibenzothiophene group, or a substituted or unsubstituted dibenzofuran group;

a substituted group comprises one or more substituent groups selected from the group consisting of heavy hydrogen, a halogen group, an alkyl group, an alkenyl group, an alkoxy group, a silyl group, an arylalkenyl group, an aryl group, a heteroaryl group, an arylamine group, a fluorenyl group, and a nitrile group; and R7 and R8 are the same as or different from each other, and are each independently a halogen group, a nitrile group, a nitro group, a hydroxy group, or an unsubstituted alkyl group.

At Column 52, Line 1, to Column 66, Line 39, please replace Claim 7 with the following claim:
7. The organic electronic device of claim 1, wherein the compound of Chemical Formula 1 has any one of the following Chemical Formulas:

[Chemical Formula 1-2]     [Chemical Formula 1-3]     [Chemical Formula 1-6]     [Chemical Formula 1-7]

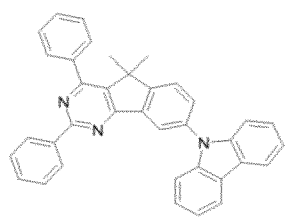 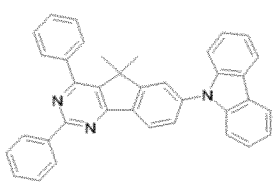 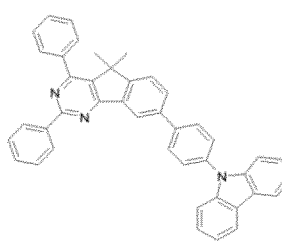 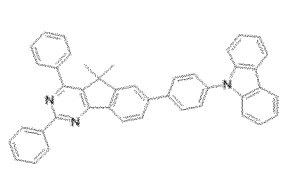

[Chemical Formula 1-10]     [Chemical Formula 1-11]     [Chemical Formula 1-14]     [Chemical Formula 1-15]